(12) United States Patent
Crouse et al.

(10) Patent No.: US 6,919,464 B1
(45) Date of Patent: Jul. 19, 2005

(54) SYNTHETIC DERIVATIVES OF 21-BUTENYL AND RELATED SPINOSYNS

(75) Inventors: Gary D. Crouse, Noblesville, IN (US); Donald R. Hahn, Zionsville, IN (US); Paul R. Graupner, Carmel, IN (US); Jeffrey R. Gilbert, Indianapolis, IN (US); Paul Lewer, Indianapolis, IN (US); Jesse L. Balcer, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/471,795
(22) PCT Filed: Mar. 21, 2002
(86) PCT No.: PCT/US02/08572
§ 371 (c)(1), (2), (4) Date: Sep. 15, 2003
(87) PCT Pub. No.: WO02/077004
PCT Pub. Date: Oct. 3, 2002

Related U.S. Application Data
(60) Provisional application No. 60/277,546, filed on Mar. 21, 2001.

(51) Int. Cl.[7] .................. C07D 313/06; A61K 31/365
(52) U.S. Cl. .................. 549/266; 549/268; 549/271; 514/28; 514/450
(58) Field of Search .................. 549/266, 268, 549/271; 514/28, 450

(56) References Cited
U.S. PATENT DOCUMENTS
6,455,504 B1 * 9/2002 Lewer et al. .................. 514/28
* cited by examiner Primary Examiner—Ba K. Trinh
(74) Attorney, Agent, or Firm—Donald Stuart

(57) ABSTRACT

Macrolide compounds produced by synthetic modification of factors produced by NRRL 30141 have insecticidal and acaricidal activity and are useful intermediates for preparing additional insecticidal and acaricidal compounds

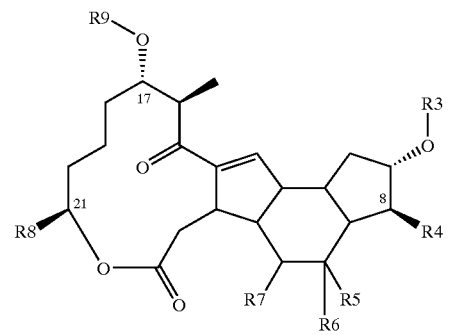

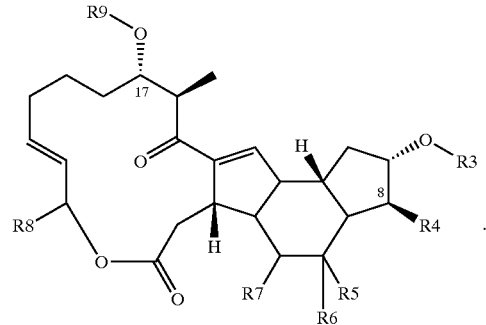

21 Claims, No Drawings

SYNTHETIC DERIVATIVES OF 21-BUTENYL AND RELATED SPINOSYNS

This application claims the benefit of provisional application Ser. No. 60/277,546 filed on Mar. 21, 2001.

FIELD OF THE INVENTION

This invention relates to compounds produced by chemical modifications of the spinosyn compounds produced by NRRL 30141 or produced by mutated strains that contain inactivated O-methyltransferase genes. The compounds have insecticidal activity.

BACKGROUND OF THE INVENTION

Fermentation product A83543 is a family of compounds, referred to as spinosyns. They are produced by certain strains of *Saccharopolyspora spinosa*. These naturally occurring materials are useful for the control of arachnids, nematodes and insects, in particular *Lepidoptera* and *Diptera* species, as described in U.S. Pat. No. 5,362,634 and corresponding European Application No. 375316 A1. A large number of chemical modifications to these spinosyn compounds have been made, as disclosed in U.S. Pat. No. 6,001,981, hereby incorporated by reference.

More recently, a new family of related macrolides (see Table 1 below) have been isolated from *Saccharopolyspora* sp. LW107129 (NRRL 30141 and mutants thereof. These compounds, which are used as staring materials in preparation of the compounds of the present invention, are disclosed in U.S. Patent Appl. No. 60/153,513, and the U.S. Patent Appl. No. 60/277,601, both of which are hereby incorporated by reference. These compounds are characterized by the presence of reactive functional groups that make further modifications possible at locations where such modifications were not feasible in previously disclosed spinosyns. The same kinds of chemical modifications disclosed in U.S. Pat. No. 6,001,981 with respect to previously known spinosyns can be carried out on the starting materials identified below in Table 1 to provide the novel insecticidal compounds of the present invention.

SUMMARY OF THE INVENTION

The present invention provides compounds of the formulae (1A) and (2A)

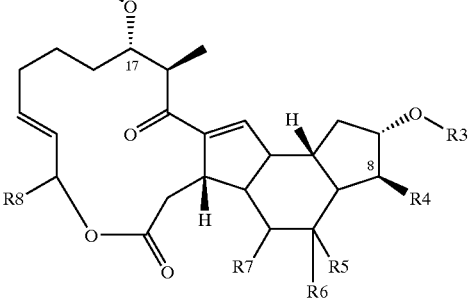

wherein
$R^3$ is a group having one of the following formulas (3a) through (3v)

(3a)

(3b)

(3c)

(3d)

(3e)

(3f)

-continued
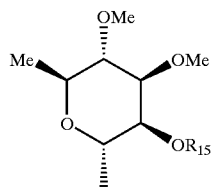 (3g)
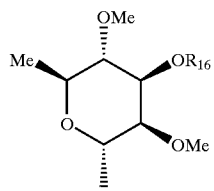 (3h)
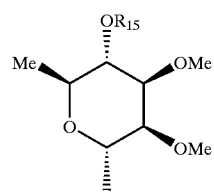 (3i)
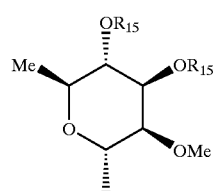 (3j)
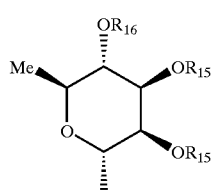 (3k)
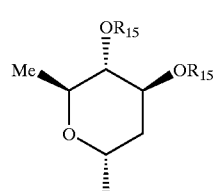 (3l)
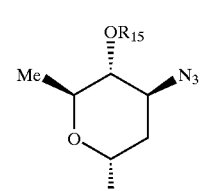 (3m)
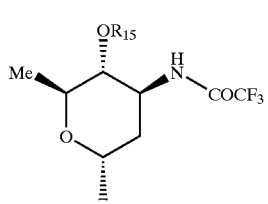 (3n)
-continued
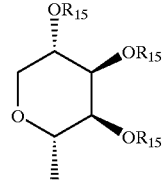 (3o)
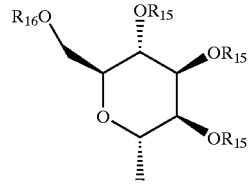 (3p)
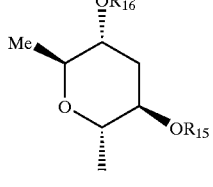 (3q)
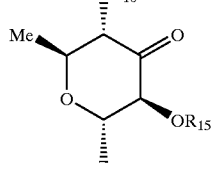 (3r)
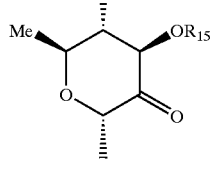 (3s)
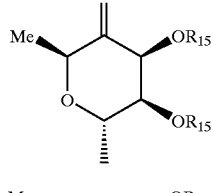 (3t)
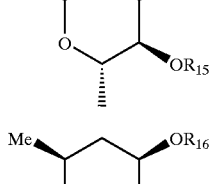 (3u)
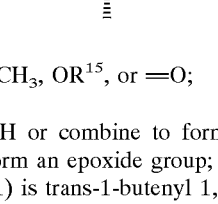 (3v)
$R^4$ is H, OH, OCH$_3$, OR$^{15}$, or =O;
$R^5$ is H or CH$_3$;
$R^6$ and $R^7$ are H or combine to form a double bond or combine to form an epoxide group;
$R^8$ in formula (1) is trans-1-butenyl 1,3-butadienyl n-butyl 3-hydroxy-1-butenyl, n-propyl-propenyl 1,2-epoxy-1- butyl, 3-oxo-1-butenyl CH$_3$CH(OCH$_3$)CH=CH—, CH$_3$CH(OR$^{15}$)=CH—, CH$_3$CH=CHCH(CH$_2$CO$_2$Me)—, or CH$_3$CH=CHCH(CH$_2$CON(Me$_2$))—

R$^9$ is H or a group having one of the following formulas (9a) through (9p):

(9a)
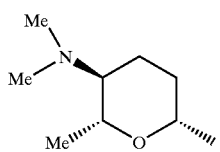

(9b)
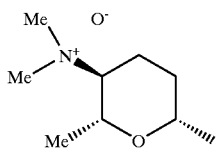

(9c)
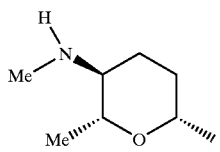

(9d)
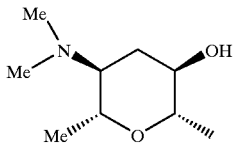

(9e)
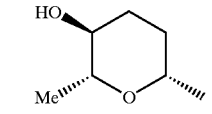

(9f)
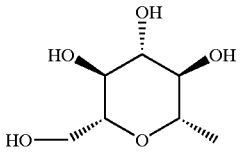

(9g)
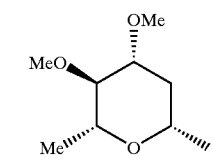

(9h)
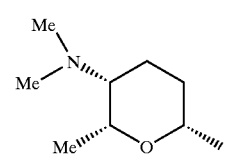

(9i)
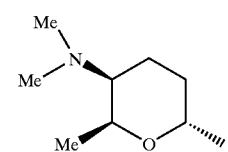

(9j)
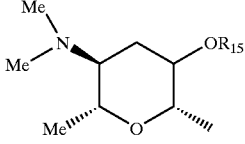

(9k)
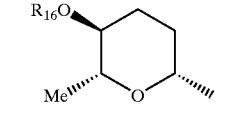

(9l)
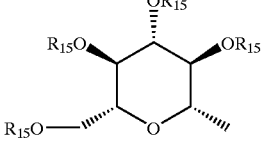

(9m)
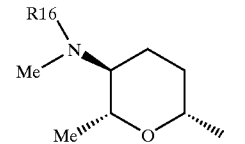

(9n)
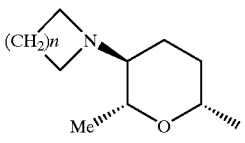

(9o)
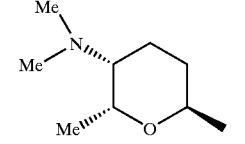

(9p)

R$^{15}$ is C2–C6 alkyl, C3–C6 branched alkyl C3–C7 cycloalkyl, C1–C6 alkoxy-C1–C6 alkyl, C1–C6 alkylthio-C1–C1 alkyl halo C1–C6 alkyl, C2–C6 alkenyl, C2–C6 alynyl formyl, C1–C6 alkylcarbonyl, or C3–C6 branched alkylcarbonyl, C3–C7-cycloalkylcarbonyl, C1–C6 alkoxy-C1–C6 alkylcarbonyl, halo C1–C6 alkylcarbonyl, C2–C6 alkenylcarbonyl, C2–C6 alkynyl-carbonyl;

R$^{16}$ in formula (9m) is C1–C6 alkyl C1–C6 alkenyl, formyl C1–C6 alkylcarbonyl, or C3–C6 branched alkylcarbonyl;

n in formula (9n) is an integer from 1 to 4;

provided that at least one of the following conditions is satisfied:

a) R$^3$ is selected from the group consisting of formulas (3g) to (3v);

b) R$^4$ is —OCH$_3$, —OR$^{15}$ or =O;

c) R$^6$ and R$^7$ are H or R$^6$ and R$^7$ combine to form an epoxide group;

d) R$^8$ is propyl n-butyl, 1,2-epoxy-1-butyl, CH$_3$C(O)CH=CH—, CH$_3$CH(OCH$_3$)CH=CH—or CH$_3$CH(OR$^{15}$)CH=CH—;

e) R⁹ is selected from the group consisting of formulas (9j) through (9p); and provided further that the compound 22,23-dihydro-rham-I is excluded.

The new compounds have activity against insects and arachnids and are also useful as intermediates for producing other insecticidal compounds.

The following classes of compounds are preferred:
1. compounds of formula (1A) wherein $R^3$ is a group of the formula (3h);
2. compounds of formula (1A) wherein $R^3$ is a group of the formula (3j);
3. compounds of formula (1A) wherein $R^3$ is a group of the formula (3k);
4. compounds of class 1, 2, or 3 wherein $R^{15}$ is ethyl, n-propyl, or i-propyl;
5. compounds of formula (1A) wherein $R^6$ and $R^7$ are both H;
6. compounds of formula (1A) wherein $R^8$ is n-butyl;
7. compounds of formula (1A) wherein $R^6$ and $R^7$ are both H and $R^8$ is n-butyl;
8. compounds of class 1, 2, 3, or 4 wherein $R^6$ and $R^7$ are both H;
9. compounds of class 1, 2, 3, 4, or 8 wherein $R^8$ is n-butyl;
10. compounds of formula (1A) wherein $R^3$ is a group of the formula (3g), (3h), (3i), (3j), or (3k), and $R^{15}$ is C2–C6 alkyl C3–C6 branched alkyl or C3–C7 cycloalkyl;
11. compounds of formula (1A) wherein $R^8$ is $CH_3CH(OCH_3)$=CH— or $CH_3CH(OR_{15})CH$=I—, where $R^{15}$ is $C_2$–$C_6$ alkyl $C_3$–$C_6$ branched alkyl, or $C_3$–$C_7$ cycloalkyl;
12. compounds of formula (1A) were $R^6$ and $R^7$ combine to form an epoxide group;
13. ketones obtained from oxidation of any free hydroxyl groups at C8, C24, C2', C3', C4', or C4";
14. compounds of any one of classes 1–13 wherein $R^9$ is a group of formula (9a);
15. 2'-, or 3'-, or 3',4'-, di-, or 2', 3', 4'-tri-$R_{15}$ rhamnosyl derivatives;
16. butenyl spinosyns wherein the sugar attached to C-9 is a 2'-, 3', or 4'-deoxy L-rhamnosyl derivative, or per-O-alkylated L-lyxose or L-mannose;
17. ethers at C-24 or C-8;
18. N-alkyl derivatives of naturally occurring amino-containing factors or of any derivatives of classes 1–13 and 15–17 prepared therefrom.

The novel compounds of the present invention are produced using starting materials obtained by culturing NRRL 30141 or a mutant thereof. Synthetic modifications within the scope of the invention include modifications to the rhamnose sugar, forosamine sugar, and to the molecule via hydrogenation, epoxidation, reduction, halogenation, and the addition of substituents on the macrocyclic lactone.

DETAILED DESCRIPTION OF THE INVENTION

The butenyl spinosyns are named in Table 1 and referred to hereinafter by the structural acronyms "for-rham-I", "for-rham-II", "for-rham-II" and derivatives thereof. In these cases I, II, and III refer to the appropriately-substituted macrolide structure (I: $R^4$=$R^5$=H; II: $R^5$=$CH_3$, $R^4$=H or OH; m: $R^5$=H, $R^4$=OH), 'for' represents the sugar at C-17 (for=forosamine), and 'rham' represents the sugar at C-9 (rham=tri-O-methylrhamnose). A second type of macrolide structure which is produced by strain NRRL 30141, with general Formula (2) having a 14-membered macrolide ring, is referred to hereinafter as "for-rham-IV".

The novel compounds of the invention are named in a similar shorthand notation. For example, (5,6-dihydro)-for-(3'-O-ethyl)rham-I consists of the 21-butenyl nucleus, with ethyl replacing the methyl group on C3'-O— and the 5,6 double bond is reduced.

As used hereinafter, the term "$C_1$–$C_6$-haloalkyl" means an alkyl group having 1 to 6 carbon atoms with one or more halogen atoms bound to the carbon atoms. "Halogen" means Cl, F, Br, or I.

In the detailed examples set forth hereinafter, all reagents and solvents were used directly as purchased firm commercial suppliers and all reactions were conducted with constant magnetic siring at ambient temperature (20–22° C.), unless otherwise noted. All reactions involving organometallic, moisture sensitive, or metal hydride reagents were conducted in commercially available dry solvents under a dry nitrogen atmosphere. Partitions, extractions, or washes with NaCl NaHCO₃, NH₄Cl, and other salts refer to saturated aqueous solutions of these salts. Reactions are typically "worked-up" by extraction of an organic solution of the products with one of the above salt solutions; the organic layer was dried with $K_2CO_3$, $Na_2SO_4$, or $MgSO_4$, filtered and evaporated in vacuo. Reversed-phase thin layer chromatography (RPTLC) was done on glass-backed octadecylsilane-bonded plates, 0.2 mm thickness from Whatman. Chromatography refers to flash chromatography and was performed on E. Merck silica gel 60 (230–400 mesh). Reversed-phase high performance liquid chromatography (RPHPLC) was performed on C18 bonded silica gel (Rainin Dynamax 60 A, 8 μm or Waters YMC). AU melting points were determined in open capillaries and are uncorrected. $^1H$ NMR and $^{13}C$ NMR spectra were determined at 300 or 600 MHz and 75 or 150 MHz respectively, in $CDCl_3$. Mass spectral data were measured via electrospray ionization (ESI). Elemental analyses were provided by analytical laboratory of Dow AgroSciences or Midwest Microlabs.

The compounds of the present invention are prepared directly or indirectly by modifying the compounds naturally produced by LW107129 or mutants thereof that contain inactivated O-methyltransferase genes. Specific examples of starting materials produced by NRRL 30141 or mutants thereof that contain inactivated O-methyltransferase genes are given in Table 1.

These compounds are specifically disclosed in U.S. Patent Appl. No. 60/153,513, and the U.S. Patent Appl. No. 60/277, 601.

TABLE 1

Butenyl spinosyns produced by *Saccharopolyspora* sp. LW107129, or by mutated strains which contain inactivated O-methyltransferase genes.

(1)

(2)

| cmpd. no. | Name | formula | R3* | R4 | R5 | R6 | R7 | R8 | R9** |
|---|---|---|---|---|---|---|---|---|---|
| 1 | for-rham-I | (1) | (3a) | H | H | double bond | | 1-butenyl | (9a) |
| 2 | N-oxy-for-rham-I | (1) | (3a) | H | H | double bond | | 1-butenyl | (9b) |
| 3 | N-desmethyl for-rham-I | (1) | (3a) | H | H | double bond | | 1-butenyl | (9c) |
| 4 | 2"-hydroxy-for-rham-I | (1) | (3a) | H | H | double bond | | 1-butenyl | (9d) |
| 5 | for-(2'-O-desmethyl rham)-I | (1) | (3b) | H | H | double bond | | 1-butenyl | (9a) |
| 6 | for-(3'-O-desmethyl rham)-I | (1) | (3c) | H | H | double bond | | 1-butenyl | (9a) |
| 7 | for-rham-II | (1) | (3a) | H | CH₃ | double bond | | 1-butenyl | (9a) |
| 8 | for-rham-III | (1) | (3a) | OH | H | double bond | | 1-butenyl | (9a) |
| 9 | 24-hydroxy-for-rham-I | (1) | (3a) | H | H | double bond | | 3-hydroxy-1-butenyl | (9a) |
| 10 | 24-hydroxy-N-desmethylfor-rham-I | (1) | (3a) | H | H | double bond | | 3-hydroxy-1-butenyl | (9c) |
| 11 | 24,25-dehydro-for-rham-I | (1) | (3a) | H | H | double bond | | 1,3-butadienyl | (9a) |
| 12 | ami-rham-I | (1) | (3a) | H | H | double bond | | 1-butenyl | (9e) |
| 13 | 3"-O-methyl-glu-rham-I | (1) | (3a) | H | H | double bond | | 1-butenyl | (9f) |
| 14 | ami-rham-III | (1) | (3a) | OH | H | double bond | | 1-butenyl | (9e) |
| 15 | mole-rham-III | (1) | (3a) | OH | H | double bond | | 1-butenyl | (9g) |
| 16 | 24-demethyl-for-rham-I | (1) | (3a) | H | H | double bond | | 1-propenyl | (9a) |
| 17 | rham-I | (1) | (3a) | H | H | double bond | | 1-butenyl | H |
| 18 | rham-II | (1) | (3a) | H | CH₃ | double bond | | 1-butenyl | H |
| 19 | rham-III | (1) | (3a) | OH | H | double bond | | 1-butenyl | H |

TABLE 1-continued

Butenyl spinosyns produced by *Saccharopolyspora* sp. LW107129, or by mutated strains which contain inactivated O-methyltransferase genes.

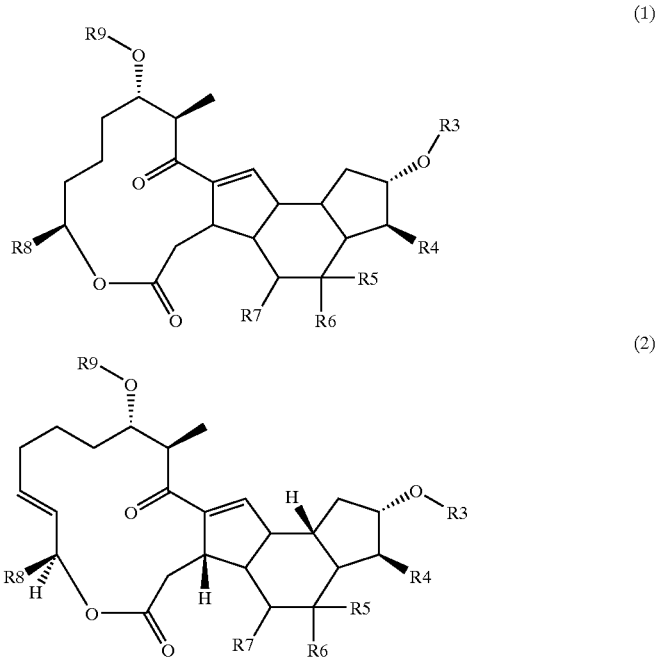

(1)

(2)

| cmpd. no. | Name | formula | R3* | R4 | R5 | R6 | R7 | R8 | R9** |
|---|---|---|---|---|---|---|---|---|---|
| 20 | 24-hydroxy-rham-I | (1) | (3a) | H | H | | double bond | 3-hydroxy-1-butenyl | H |
| 21 | 24-hydroxy-rham-III | (1) | (3a) | OH | H | | double bond | 3-hydroxy-1-butenyl | H |
| 22 | 24,25-dehydro-rham-I | (1) | (3a) | H | H | | double bond | 1,3-butadienyl | H |
| 23 | 22,23-dihydro-rham-I | (1) | (3a) | H | H | | double bond | n-butyl | H |
| 24 | (4'-N-desmethyl-1'',4''-diepi-for)-rham-I | (1) | (3a) | H | H | | double bond | 1-butenyl | (9h) |
| 25 | 5''-epifor-rham-I | (1) | (3a) | H | H | | double bond | 1-butenyl | (9i) |
| 26 | 24,25-dehydro-for-rham-III | (1) | (3a) | OH | H | | double bond | 1,3-butadienyl | (9a) |
| 27 | 8-OH-for-rham II | (1) | (3a) | OH | CH$_3$ | | double bond | 1-butenyl | (9a) |
| 28 | 24-desmethyl-for-rham-III | (1) | (3a) | OH | H | | double bond | 1-propenyl | (9a) |
| 29 | 2'-O-desmethyl rham-I | (1) | (3b) | H | H | | double bond | 1-butenyl | H |
| 30 | 3'-O-desmethyl rham-I | (1) | (3c) | H | H | | double bond | 1-butenyl | H |
| 31 | for-rham-IV | (2) | (3a) | H | H | | double bond | ethyl | (9a) |
| 32 | for-(4'-O-desmethyl-rham)-I | (1) | (3d) | H | H | | double bond | 1-butenyl | (9a) |
| 33 | for-(2',3',4'-tri-O-desmethyl-rham)-I | (1) | (3f) | H | H | | double bond | 1-butenyl | (9a) |
| 34 | for-(4'-O-desmethyl-rham)-III | (1) | (3d) | OH | H | | double bond | 1-butenyl | (9a) |
| 35 | (4''-N-desmethyl-for)-(4'-O-desmethyl-rham)-I | (1) | (3d) | H | H | | double bond | 1-butenyl | (9c) |
| 36 | for-(4'-O-desmethyl-rham)-II | (1) | (3d) | H | CH$_3$ | | double bond | 1-butenyl | (9a) |
| 37 | for-(3',4'-di-O-desmethyl-rham)-I | (1) | (3e) | H | H | | double bond | 1-butenyl | (9a) |

TABLE 1-continued

Butenyl spinosyns produced by *Saccharopolyspora* sp. LW107129, or by mutated strains which contain inactivated O-methyltransferase genes.

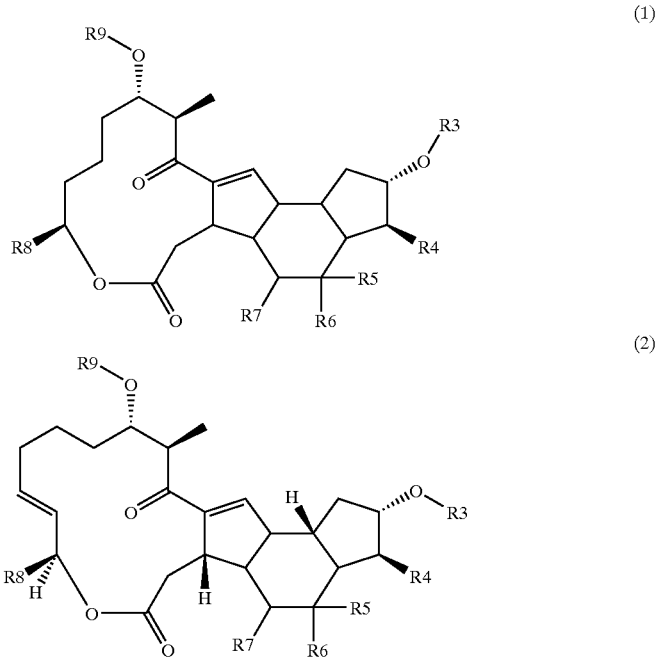

(1)

(2)

| cmpd. no. | Name | formula | R3* | R4 | R5 | R6 | R7 | R8 | R9** |
|---|---|---|---|---|---|---|---|---|---|
| 38 | 24-desmethyl-rham-I | (1) | (3a) | H | H | double bond | | 1-propenyl | H |
| 39 | (4'-O-desmethyl-rham)-I | (1) | (3d) | H | H | double bond | | 1-butenyl | H |
| 40 | for-(3',4'-di-O-desmethyl-rham)-III | (1) | (3e) | OH | H | double bond | | 1-butenyl | (9a) |
| 41 | for-(3'-O-desmethyl-rham)-III | (1) | (3c) | OH | H | double bond | | 1-butenyl | (9a) |
| 42 | (N-oxy-for)-(3'-4'-di-O-desmethyl-rham)-I | (1) | (3e) | H | H | double bond | | 1-butenyl | (9b) |
| 43 | 24-desmethyl-for-(3',4'-di-O-desmethyl-rham)-I | (1) | (3e) | H | H | double bond | | 1-propenyl | (9a) |
| 44 | for-(3',4'-di-O-desmethyl-rham)-II | (1) | (3e) | H | CH$_3$ | double bond | | 1-butenyl | (9a) |
| 45 | 24-hydroxy-for (3'-O-desmethyl-rham)-I | (1) | (3c) | H | H | double bond | | 3-hydroxy-1-butenyl | (9a) |
| 46 | N-desmethyl for-((3'-O-desmethyl-rham)-I | (1) | (3c) | H | H | double bond | | 1-butenyl | (9c) |

*formulas (3a)–(3f) are as defined above.
**formulas (9a)–(9i) are as defined above.

The butenyl-spinosyn starting materials can be prepared by culturing one of the following strains of *Saccaropolyspora* sp. that were deposited on the dates indicated in accordance with the terms of the Budapest treaty at the Midwest Area Regional Research Center, Agricultural Research Service, United States Department of Agriculture, 815 North University Street, Peoria, Ill. 61604:

| strain | deposit number | deposit date |
|---|---|---|
| LW107129 | NRRL 30141 | Jun. 9, 1999 |
| 30141.2 | NRRL 30424 | Mar. 8, 2001 |
| 30141.3 | NRRL 30423 | Mar. 8, 2001 |
| 30141.4 | NRRL 30422 | Mar. 8, 2001 |

-continued

| strain | deposit number | deposit date |
|---|---|---|
| 30141.5 | NRRL 30438 | Mar. 15, 2001 |
| 30141.8 | NRRL 30421 | Mar. 8, 2001 |
| 30141.13 | NRRL 30437 | Mar. 15, 2001 |

The compounds of the invention are prepared from the butenyl-spinosyn starting materials using any of the various synthetic schemes described in U.S. Pat. No. 6,001,981. Examples of such conversions are listed in the following schemes, although it should be understood by one skilled in the art of synthesis that the examples are not exhaustive.

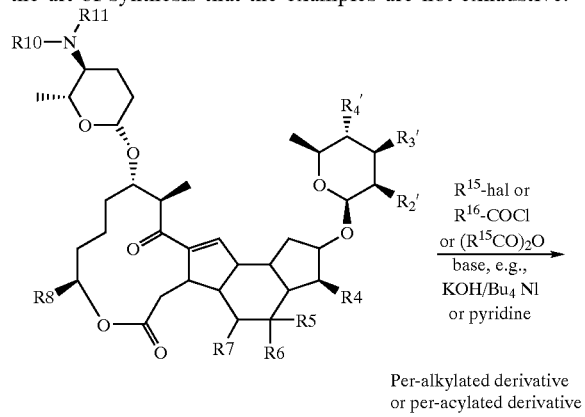

Per-alkylated derivative
or per-acylated derivative

Compounds of formula (A) wherein one or more of $R^4$, $R^{2'}$, $R^{3'}$, and $R^{4'}$ is OH, or wherein R8 is 3-hydroxy-1-butenyl or 3-hydroxy-1-butyl, can be converted into the corresponding O-alkyl ethers or O-acyl esters using any of a variety of alkylating and acylating reagents. For example, use of powdered potassium hydroxide and a quaternary ammonium or phosphonium salt such as tetra-n-butylammonium iodide and an alkylating agent of the formula $R^{15'}$-halo, where $R^{15'}$ is $C_1$–$C_6$ alkyl, C3–C6 branched alkyl $C_3$–$C_7$ cycloalkyl, C1–C6 alkoxy-C1–C6 alkyl, halo C1–C6 alkyl, C2–C6 alkenyl, or C2–C6 alkynyl; and halo is F, Cl, Br, or I, either without additional solvent or by use of dichloromethane or chloroform or DMSO, will convert any available —OH group into the corresponding —$OR^{15'}$ derivative. An example of an alkylating agent of formula $R^{15'}$-halo is bromoethane. Alternatively, reaction with an alkyl or aryl acid chloride or anhydride of the formula $R^{15'}COCl$ or $R^{15'}(CO)_2O$, where $R^{15'}$ is as defined above, in the presence of a base such as pyridine, results in acylation of any free —OH groups.

Examples of compounds that can be produced in accordance with Scheme A are shown in Table A.

TABLE A

Examples of compounds prepared by Scheme A.

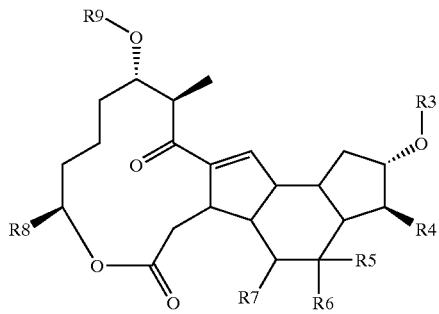

| cmpd. no. | SM* | formula | R3 | R4 | R5 | R6 | R7 | R8 | R9 |
|---|---|---|---|---|---|---|---|---|---|
| A1 | 5 | 1A | OMe / Me, OMe, OEt (sugar) | H | H | Double bond | | 1-butenyl | (9a) |

TABLE A-continued

Examples of compounds prepared by Scheme A.

| cmpd. no. | SM* | formula | R3 | R4 | R5 | R6 | R7 | R8 | R9 |
|---|---|---|---|---|---|---|---|---|---|
| A2 | 6 | 1A | Me, OMe, OEt, OMe (pyranose) | H | | H | Double bond | 1-butenyl | (9a) |
| A3 | 37 | 1A | Me, OEt, OEt, OMe (pyranose) | H | | H | Double bond | 1-butenyl | (9a) |
| A4 | 20 | 1A | (3a) | H | | H | Double bond | 3-ethoxy-1-butenyl | (9a) |
| A5 | 8 | 1A | (3a) | OC$_2$H$_5$ | | H | Double bond | 1-butenyl | (9a) |
| A6 | 6 | 1A | Me, OMe, O-nPr, OMe (pyranose) | H | | H | Double bond | 1-butenyl | (9a) |
| A7 | 6 | 1A | Me, OMe, O-nBu, OMe (pyranose) | H | | H | Double bond | 1-butenyl | (9a) |
| A8 | 6 | 1A | Me, OMe, O-allyl, OMe (pyranose) | H | | H | Double bond | 1-butenyl | (9a) |

TABLE A-continued

Examples of compounds prepared by Scheme A.

| cmpd. no. | SM* | formula | R3 | R4 | R5 | R6 | R7 | R8 | R9 |
|---|---|---|---|---|---|---|---|---|---|
| A9 | 6 | 1A | (sugar with OMe, Me, O-propargyl, OMe) | H | H | Double bond | | 1-butenyl | (9a) |
| A10 | 6 | 1A | (sugar with OMe, Me, O-isopropyl, OMe) | H | H | Double bond | | 1-butenyl | (9a) |
| A11 | 6 | 1A | (sugar with OMe, Me, O-isobutyl, OMe) | H | H | Double bond | | 1-butenyl | (9a) |
| A12 | 6 | 1A | (sugar with OMe, Me, O-CH₂OMe, OMe) | H | H | Double bond | | 1-butenyl | (9a) |
| A13 | 6 | 1A | (sugar with OMe, Me, OAc, OMe) | H | H | Double bond | | 1-butenyl | (9a) |

TABLE A-continued
Examples of compounds prepared by Scheme A.
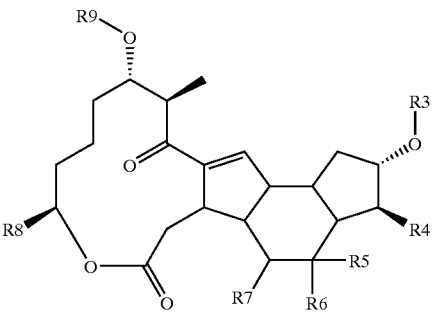
| cmpd. no. | SM* | formula | R3 | R4 | R5 | R6 | R7 | R8 | R9 |
|---|---|---|---|---|---|---|---|---|---|
| A14 | B18 | 1A | Me—(OH, OMe, OMe) pyran | H | H | H | H | n-Bu | (9a) |
| A15 | B12 | 1A | Me—(OMe, O-nC$_2$H$_5$, OMe) pyran | H | H | H | H | n-Bu | (9a) |
| A16 | B12 | 1A | Me—(OMe, O-nC$_3$H$_7$, OMe) pyran | H | H | H | H | n-Bu | (9a) |
| A17 | B12 | 1A | Me—(OMe, O-nC$_4$H$_9$, OMe) pyran | H | H | H | H | n-Bu | (9a) |
| A18 | B12 | 1A | Me—(OMe, O-nC$_5$H$_{11}$, OMe) pyran | H | H | H | H | n-Bu | (9a) |
| A19 | 45 | 1A | Me—(OMe, O-nC$_2$H$_5$, OMe) pyran | H | H | H | Double bond | 3-OEt-1-butenyl | (9a) |

TABLE A-continued

Examples of compounds prepared by Scheme A.

| cmpd. no. | SM* | formula | R3 | R4 | R5 | R6 | R7 | R8 | R9 |
|---|---|---|---|---|---|---|---|---|---|
| A20 | 45 | 1A | Me, OMe, O-C₃H₇, OMe (pyranose) | H | H | | Double bond | 3-O-nPr-1-butenyl | (9a) |
| A21 | 45 | 1A | Me, OMe, O-C₄H₉, OMe (pyranose) | H | H | | Double bond | 3-O-nBu-1-butenyl | (9a) |
| A22 | B11 | 1A | Me, OMe, O-C₂H₅, OMe (pyranose) | H | H | H | H | 1-butenyl | (9a) |
| A23 | B11 | 1A | Me, OMe, O-nC₃H₇, OMe (pyranose) | H | H | H | H | 1-butenyl | (9a) |
| A24 | B11 | 1A | Me, OMe, O-C₄H₉, OMe (pyranose) | H | H | H | H | 1-butenyl | (9a) |
| A25 | B17 | 1A | (3a) | H | H | H | H | 3-OEt-1-butyl | (9a) |

TABLE A-continued

Examples of compounds prepared by Scheme A.

| cmpd. no. | SM* | formula | R3 | R4 | R5 | R6 | R7 | R8 | R9 |
|---|---|---|---|---|---|---|---|---|---|
| A26 | B18 | 1A | (methyl-dioxolane-pyranose with OMe) | H | H | H | H | n-Bu | (9a) |
| A27 | G1 | 1A | (Me, OMe, OEt, OMe pyranose) | H | H | Double bond | CH$_3$CH=CHCH(CH$_2$CO$_2$Me)- | | (9a) |
| A28 | G2 | 1A | (Me, OMe, OEt, OMe pyranose) | H | H | Double bond | CH$_3$CH=CHCH(CH$_2$C(O)NMe$_2$)- | | (9a) |

*starting material

EXAMPLE 1

Synthesis of for-(3'-O-ethyl rham)-I (Compound A2)

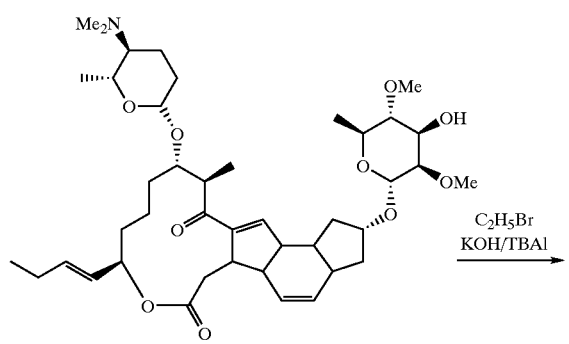
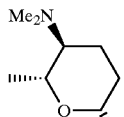
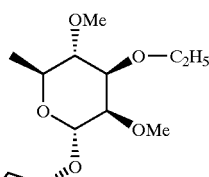

To a solution of for-(3'-O-desmethylrham)-I (Compound 6)(6.8 mg, 0.0091 mmol) in 1 ml of ethyl bromide was added 10 mg (cat) of powdered potassium hydroxide and tetra-n-Bu ammonium iodide (KOH/TBAI) (10:1). After 24 h, TLC indicated incomplete reaction, so another 10 mg aliquot of KOH/TBAI was added. After another 24 h, the solution was diluted with 4 ml of ether and the solution was filtered and concentrated to give 5.0 mg of for-(3'-O-ethylrham)-I (Compound A2). $^1$H NMR δ 3.65, 3.72 (two multiplets, —OCH$_2$CH$_3$) M.S. 772.5 (M+1).

EXAMPLE 2

Synthesis of for-(3'-O-n-propyl rham)-I (Compound A6)

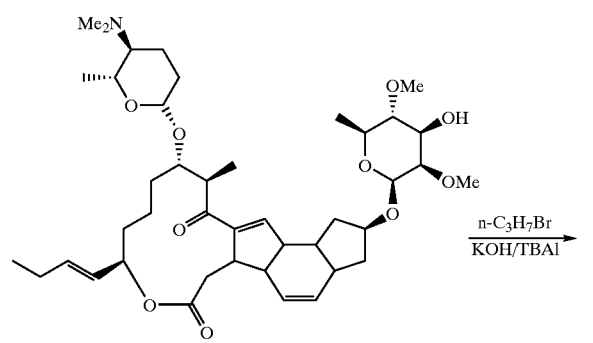

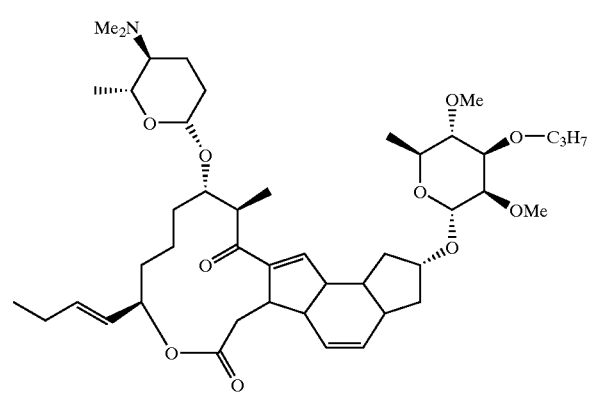

To a solution of for-(3'-O-desmethylrham)-I (Compound 6)(54 mg, 0.073 mmol) in 2 ml of n-propyl bromide was added 100 mg (cat) of powdered potassium hydroxide and tetra-n-Butylammonium iodide (KOH/TBAI) (10:1). After 24 h, the solution was diluted with 4 ml of ether and the solution was filtered and concentrated to give 5.0 mg of for-(3'-O-n-propyl rham)-I (Compound A6). M.S. 786.5 (M+1).

EXAMPLE 3

Synthesis of for-(2'-O-ethylrham)-I (Compound A1)

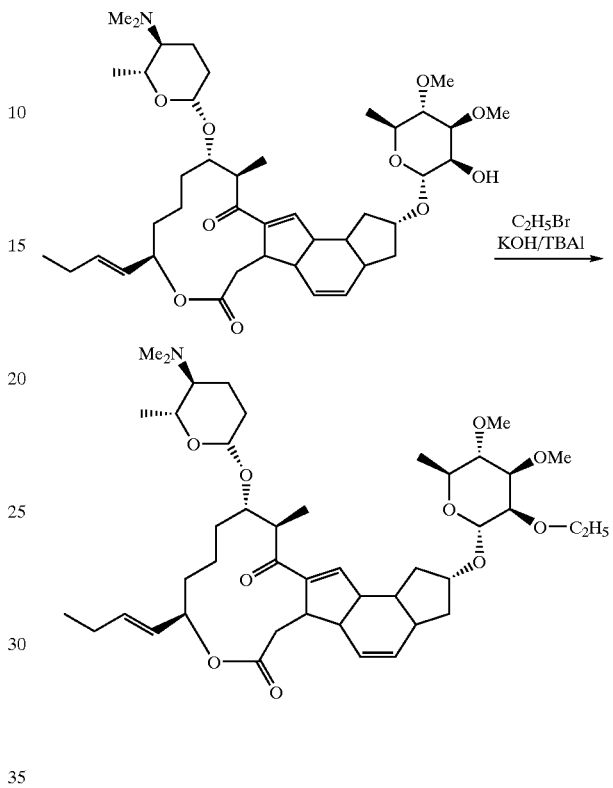

To a solution of for-(2'-O-desmethylrham)-I (Compound 5)(6.2 mg, 0.008 mmol) in 1 ml of ethyl bromide was added 10 mg (cat) of powdered KOH/TBAI (10:1). After 24 h, tlc indicated the reaction was complete. The solution was diluted with 4 ml of ether and the solution was filtered and concentrated to give 5.0 mg of for-(2'O-ethylrham)-I (Compound A1). $^1$H NMR δ 3.70 (q, J=7.5 Hz, 2K OCH$_3$); M.S. 772.5, 773.5 (M, M+1).

EXAMPLE 4

Synthesis of (24-O-thyl) for-rham-I (Compound A4)

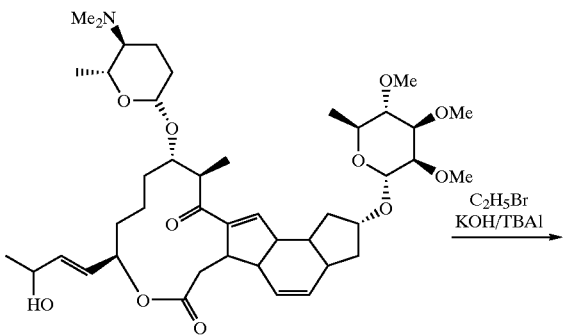

-continued

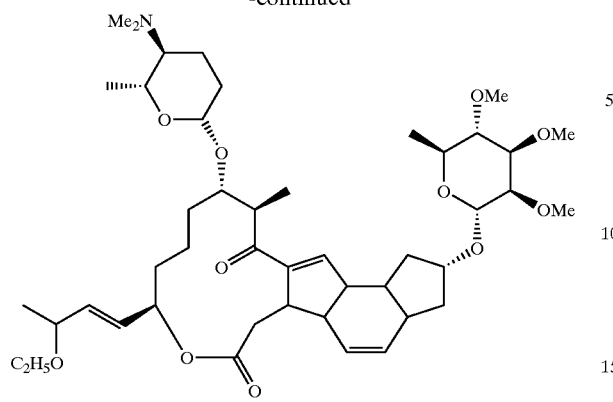

To a solution of 24-hydroxy-for-rham-III (Compound 20)(10.3 mg, 0.013 mmol) in 1 ml of ethyl bromide was added 10 mg (cat) of powdered KOH/TBAI (10:1). After 28 h, tlc indicated the reaction was complete. The solution was diluted with 4 ml of ether and the solution was filtered and concentrated to give 9.0 mg of (24-O-ethyl)-for-rham-III (Compound A4). $^1$H NMR 3.79 (m, 1H, C24-CH; 5.5 (narrow m, 2H, 22-CH= & 23-CH=).

EXAMPLE 5

Synthesis of (8-O-ethyl)-for-rham-III (Compound A5)

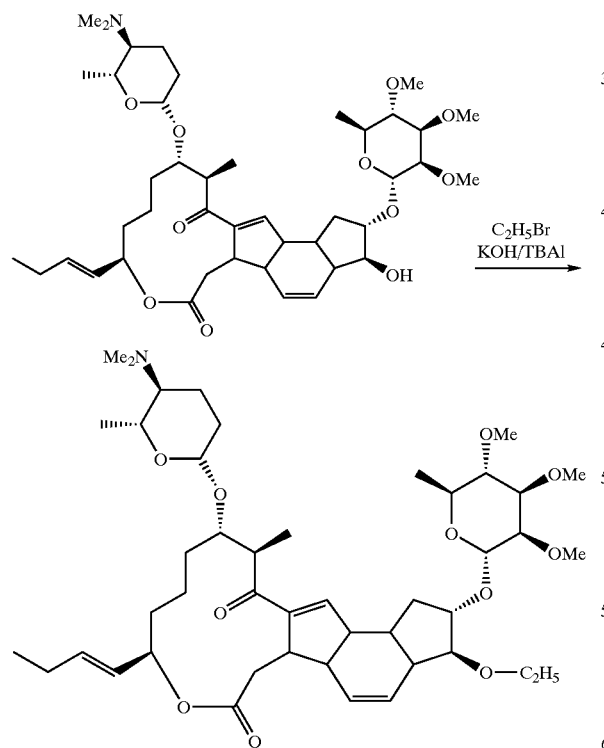

To a solution of for-rham-1 (Compound 8)(20 mg, 0.026 mmol) in 1 ml of ethyl bromide was added 25 mg (cat) of powdered KOH/TBAI (10:1). After 28 h, TLC indicated the reaction was complete. The solution was diluted with 4 ml of ether and the solution was filtered and concentrated to give 17.0 mg of 8-O-ethyl-for-rham-m (Compound A5). $^1$H NMR δ 3.69 (d, 1H, C8-CH; M.S. 802.5 (M+1).

EXAMPLE 6

Synthesis of for-(3,4'-bis-O-ethylrham)-I (Compound A3)

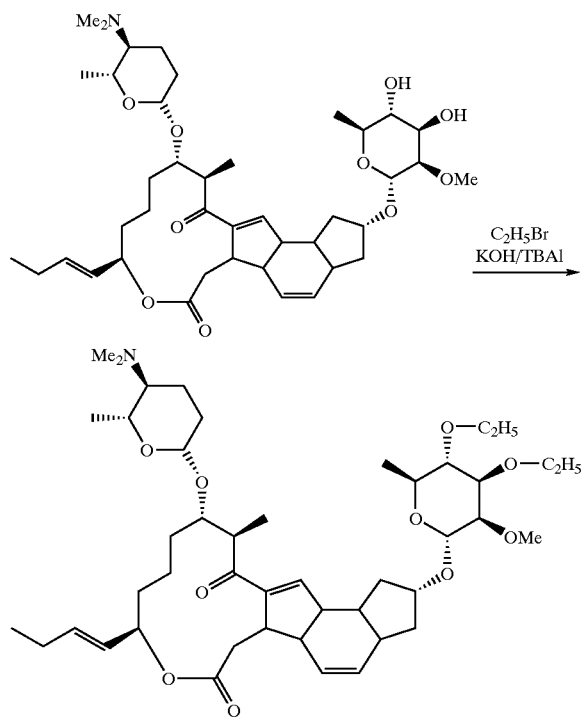

To a solution of for-(3,4'-bis-O-desmethylrham-I (Compound 37)(23 mg, 0.0091 mmol) in 1 ml of ethyl bromide was added 10 mg (cat) of powdered potassium hydroxide and tetra-n-Butylammonium iodide (KOH/TBAI) (10:1). After 24 h, the solution was diluted with 4 ml of other and the solution was filtered and concentrated to give 23 mg of for-(3',4'-bis-O-ethylrham)-I (Compound A3). 1H NMR δ3.8 and 3.9 (two m, 4H total, C3'- and C4'-OCH$_2$—).

EXAMPLE 7

Synthesis of (24-O-n-butyl)-for-(3'-O-n-butyl rham)-I (Compound A21)

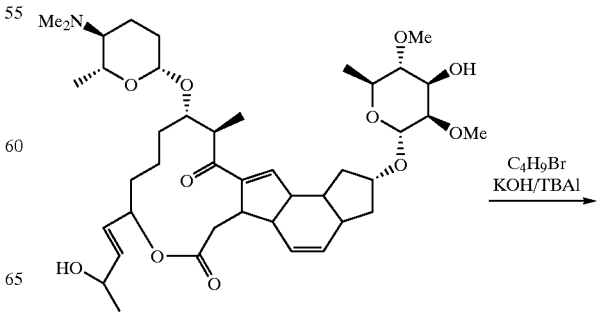

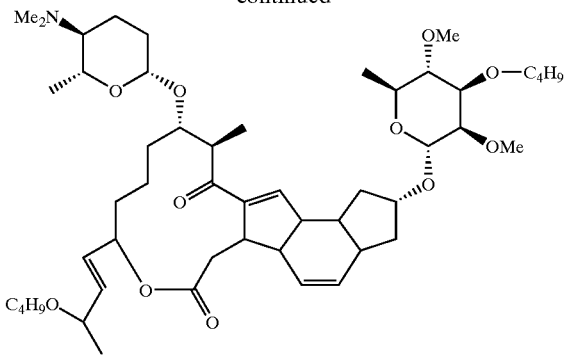

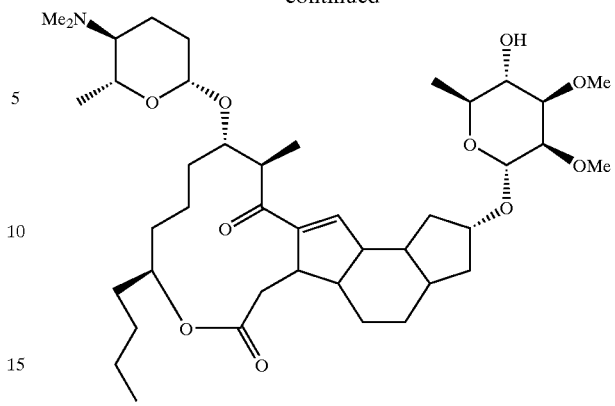

To a solution of 24-hydroxy-for-(3'-O-desmethylrham)-I (58 mg, 0.076 mmol) in 0.58 ml of butyl bromide was added 58 mg (cat) of powdered KOH/TBAI (10:1). After 48 h, tlc indicated the reaction was complete. The solution was diluted with 10 ml of ethyl acetate and washed with 10 ml of saturated NaHCO3 solution. The organic layer was dried and concentrated to give 65.0 mg of (24-O-n-butyl)-for-(3'-O-n-butyl rham)-L MS. M+1 ion at 873.

EXAMPLE 8

Synthesis of 5,6,22,23-tetrahydro for-(4'-O-desmethylrham)-I (Compound A14)

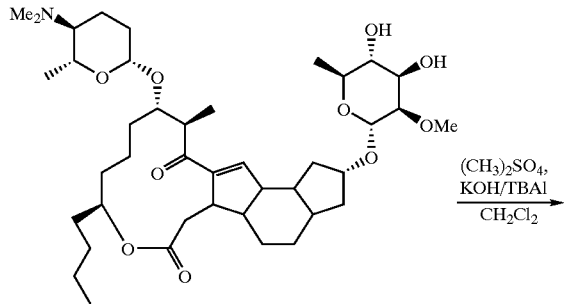

A stirred and cooled (5° C.) solution of 5,6,22,23-tetrahydro-for-(3',4'-O-desmethylrham)-I (0.12 g, 0.16 mmol) in 6 mL of dichloromethane was added 150 mg of powdered KOH/TBAI (10:1) and 20 mg (0.16 mmol) of dimethyl sulfate. The solution was allowed to warm to ambient temperature and stirred overnight, then it was diluted with 10mL of diethyl ether, filtered and concentrated. Chromatography (reverse-phase, 80–95% MeOH-$H_2O$ gradient) gave 15.5 mg of pure 5,6,22,23-tetrahydro-for-(4-O-desmethylrham)-I as a colorless foam (M.S. M+1 ion at 748.4), 12 mg of 5,6,22,23 tetrahydro-for-3'-O-desmethylrham)-I, and 3.5 mg of 5,6,22,23-tetrahydro-for-(3',4'-methylenedioxyrham)-I (M.S. M+1 ion at 747.4).

Scheme B, Hydrogenation of Double Bonds

The double bonds at positions 5,6 and 22,23 of Compounds listed in Table 1 can be selectively or wholly reduced to single bonds by using any of a variety of hydrogenating agents. Specifically, use of hydrogen and a heterogeneous catalyst such as palladium on carbon, or a homogeneous catalyst such as Wilkinson's catalyst, in a solvent such as toluene or ethanol, results in reduction of any or all of the double bonds in the molecule, depending on the severity of the conditions. Hydrogenation under heterogeneous catalytic conditions shows a preference for reduction of the 22,23-double bond. Conversely, hydrogenation using homogeneous catalysis results in preferential reduction of the 5,6-double bond

SCHDEME B.

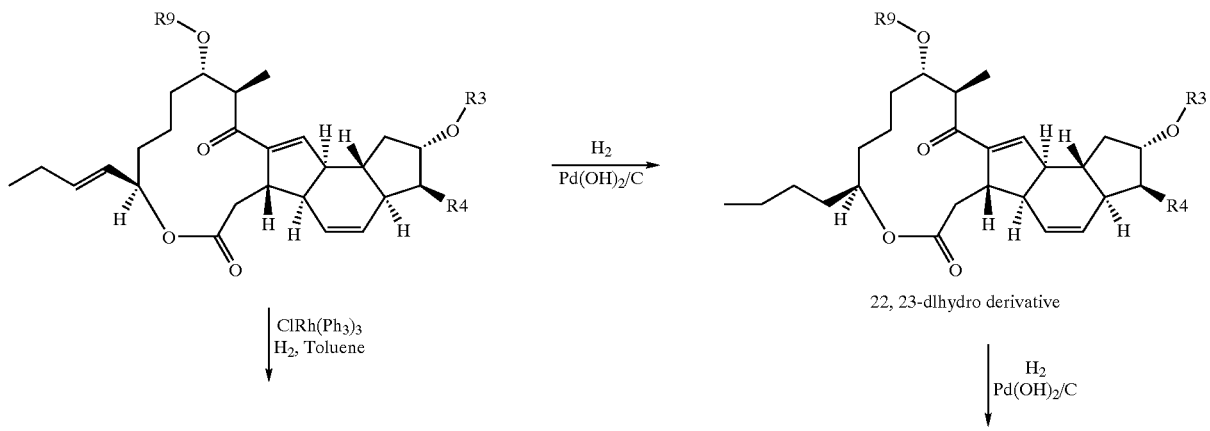

-continued
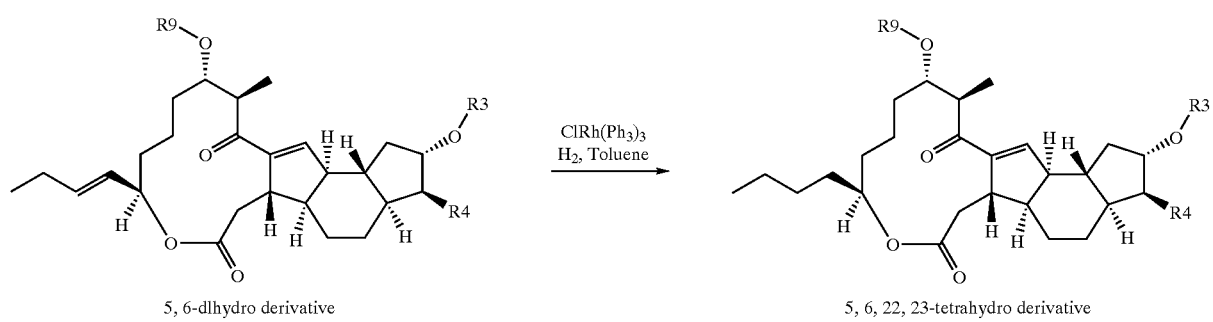
5, 6-dihydro derivative → (ClRh(Ph₃)₃, H₂, Toluene) → 5, 6, 22, 23-tetrahydro derivative
TABLE B
Examples of compounds obtainable using SCHEME B
(1A)
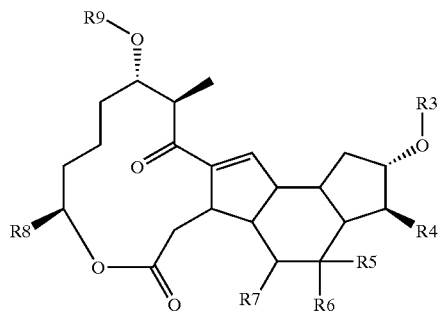
(2A)
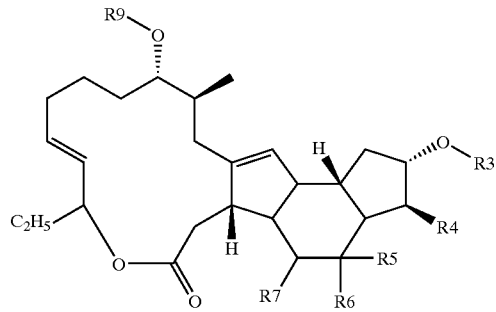
| cmpd no. | SM* | Formula | $R^3$ | $R^4$ | $R^5$ | $R^6$ | $R^7$ | $R^8$ | $R^9$ |
|---|---|---|---|---|---|---|---|---|---|
| B1 | A1 | 1A | Me-(pyranose with OMe, OMe, OEt) | H | H | H | H | n-Bu | (9a) |
| B2 | A3 | 1A | Me-(pyranose with OEt, OEt, OMe) | H | H | H | H | n-Bu | (9a) |
| B3 | 1 | 1A (3a) | | H | H | H | H | n-Bu | (9a) |
| B4 | 1 | 1A (3a) | | H | H | Double Bond | | n-Bu | (9a) |

TABLE B-continued
Examples of compounds obtainable using SCHEME B
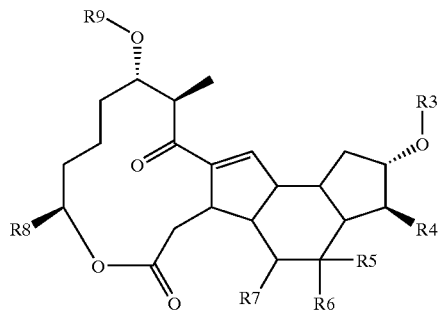
(1A)
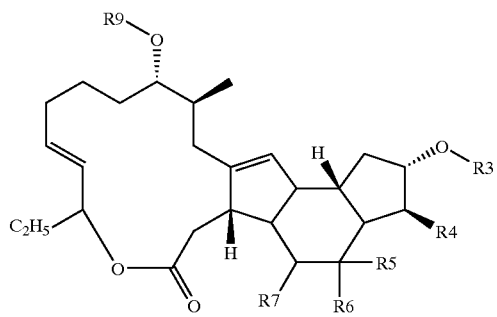
(2A)
| cmpd no. | SM* | Formula | $R^3$ | $R^4$ | $R^5$ | $R^6$ | $R^7$ | $R^8$ | $R^9$ |
|---|---|---|---|---|---|---|---|---|---|
| B5 | A2 | 1A | ![sugar with OMe, Me, OEt, OMe] | H | H | Double Bond | | n-Bu | (9a) |
| B6 | 8 | 1A | (3a) | OH | H | H | H | n-Bu | (9a) |
| B7 | 1 | 1A | (3a) | H | H | H | H | 1-butenyl | (9a) |
| B8 | 8 | 1A | (3a) | OH | H | H | H | 1-butenyl | (9a) |
| B9 | 16 | 1A | (3a) | H | H | Double Bond | | n-Pr | (9a) |
| B10 | 31 | 2A | (3a) | H | H | H | H | Et | (9a) |
| B11 | 6 | 1A | ![sugar with OMe, Me, OH, OMe] | H | H | H | H | 1-butenyl | (9a) |
| B12 | 6 | 1A | ![sugar with OMe, Me, OH, OMe] | H | H | H | H | n-Bu | (9a) |

TABLE B-continued
Examples of compounds obtainable using SCHEME B
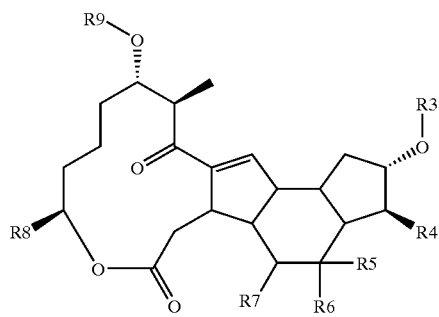
(1A)
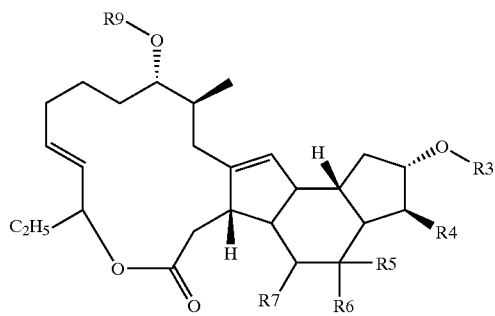
(2A)
| cmpd no. | SM* | Formula | R³ | R⁴ | R⁵ | R⁶ | R⁷ | R⁸ | R⁹ |
|---|---|---|---|---|---|---|---|---|---|
| B13 | A19 | 1A | (sugar with OMe, OC₂H₅, OMe, Me) | H | H | H | H | 3-(OC₂H₅)-1-butyl | (9a) |
| B14 | A20 | 1A | (sugar with OMe, OnC₃H₇, OMe, Me) | H | H | H | H | 3-(O-nC₃H₇)-1-butyl | (9a) |
| B15 | A21 | 1A | (sugar with OMe, OnC₄H₉, OMe, Me) | H | H | H | H | 3-(O-nC₄H₉)-1-butyl | (9a) |
| B16 | 9 | 1A | (3a) | H | H | H | H | 3-oxo-1-butyl | (9a) |
| B17 | 9 | 1A | (3a) | H | H | H | H | 3-hydroxy-1-butyl | (9a) |

TABLE B-continued
Examples of compounds obtainable using SCHEME B
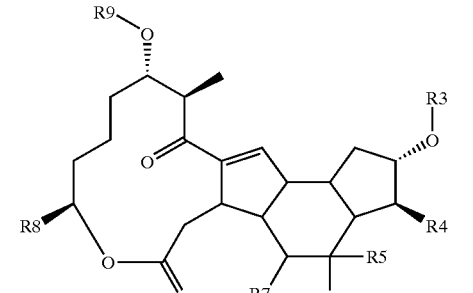
(1A)
(2A)
| cmpd no. | SM* | Formula | R³ | R⁴ | R⁵ | R⁶ | R⁷ | R⁸ | R⁹ |
|---|---|---|---|---|---|---|---|---|---|
| B18 | 37 | 1A | 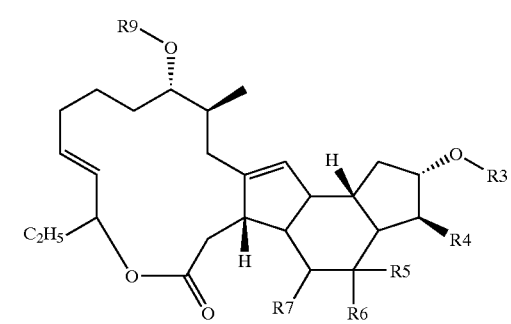 OH | H | H | H | H | n-Bu | (9a) |
*SM = starting material
EXAMPLE 9
Synthesis of 5,6-dihydro-for-(3'-O-desmethylrham)-I (Compound B11) and 5,6,22,23-tetrahydro-for-(3'-O-desmethylrham)(*Compound B*12)
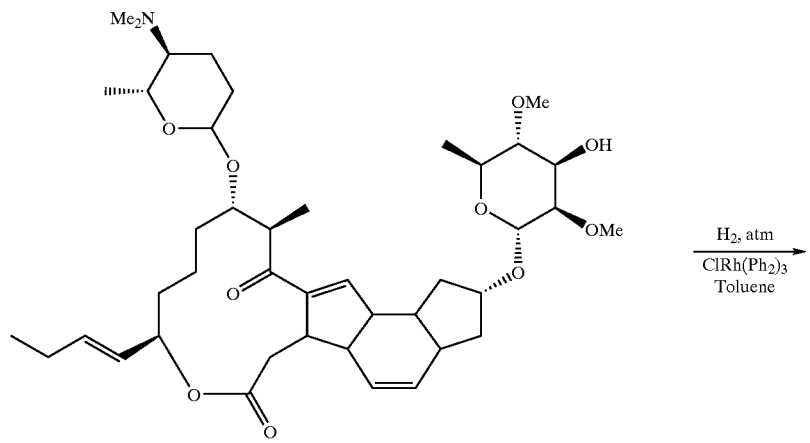

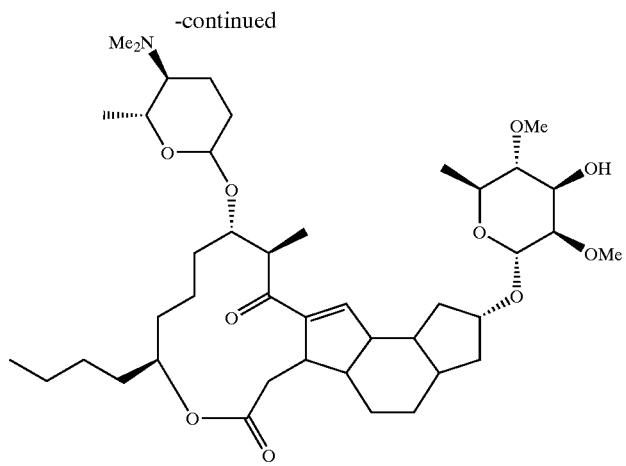

To a solution of for-3'-O-desmethyl)-rham-I)(Compound 6) (5.5 g, 7.4 mmol) in 20 mL of toluene and 15 mL of EtOH was added 200 mg (cat) of Wilkinson's catalyst. The solution was deoxygenated using a stream of nitrogen then hydrogenated at atmospheric pressure and 50° C. for 20 h, then the solution was cooled, concentrated and chromatographed (reverse-phase YMC column), eluting with a 43.5:43.5:17 solution of MeOH:acetonitrile:water (containing 0.2% NH$_4$OAc). The product-containing fractions were combined and concentrated to give 3.5 g of 5,6,22,23-tetrahydro-for-(3'-O-desmethylrham)-I (Compound B12) as a tan solid foam ($^1$H NMR C21-CH proton at δ 4.70) and 1.1 grams of 5,6-dihydro-for-(3'-O-desmethylrham)-I (Compound B11),mp 140° C., $^1$H NMR C21-CH proton at δ 5.03 and 4.7, corresponding to B11 and B12, respectively).

EXAMPLE 10

Synthesis of 5,6,22,23-tetrahydro-for-(3',4'-bis-O-ethylrham)-I (Compound B2)

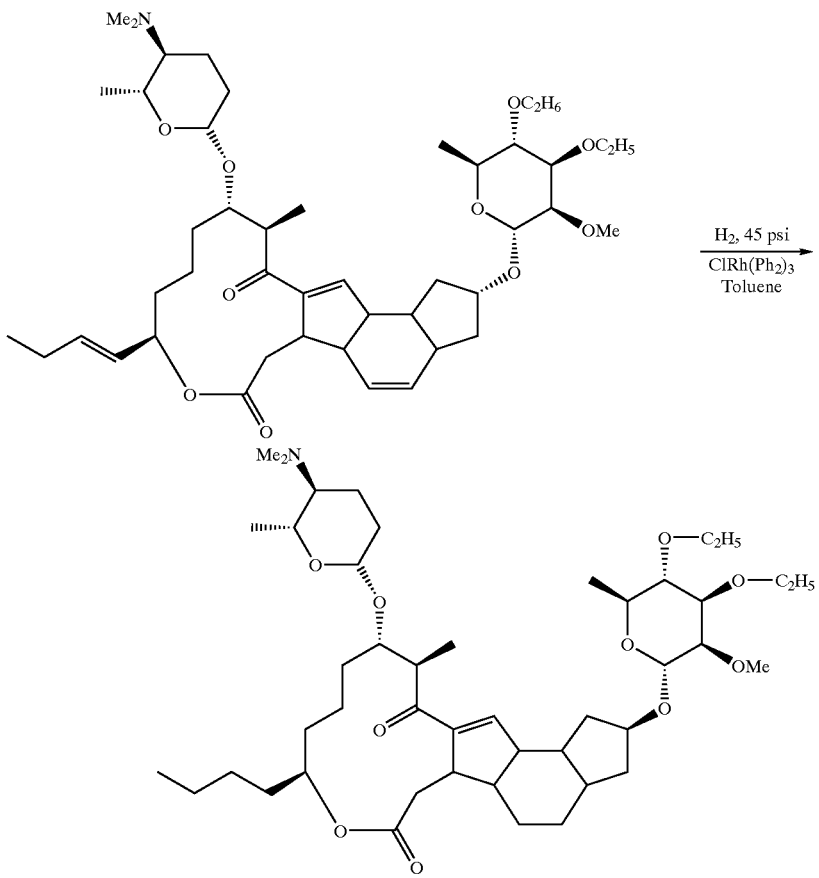

To a solution of for-(3',4'-bis-O-ethylrham)-I (Compound A3)(23 mg, 0.072 mmol) in 5 mL of toluene was added 10 mg (cat) of Wilkinson's catalyst. The solution was hydrogenated on a Parr apparatus at 45 psi for 42 h, then the solution was concentrated and chromatographed (silica gel), eluting with a $CH_2Cl_2$—MeOH gradient (0–3%). The product-containing fractions were combined and concentrated to give 9.7 mg of pure 5,6,22,23-tetrahydro-for-(3',4'-bis-O-ethylrham)-I (Compound B2) as a tan solid foam. M.S. 790.7 (M+1).

EXAMPLE 11

Synthesis of 5,6,22,23-tetrahydro-for-rham-I (Compound B3)

To a solution of for-rham-I (55 mg, 0.072 mmol) in 5 mL of toluene was added 25 mg (cat) of Wilkinson's catalyst. The solution was hydrogenated on a Parr apparatus at 45 psi for 42 h, then the solution was concentrated and chromatographed (silica gel), eluting with a $CH_2Cl_2$—MeOH gradient (0–3%). The product-containing fractions were combined and concentrated to give 32 mg of pure 5,6,22,23-tetrahydro-for-rham-I (Compound B4) as a tan solid foam M.S. M+1 ion at 763.02, NMR δ 6.88 (s, 1H, 13-CH, 4.85 (s, 1H, 1'-CH, 4.71(m, 1H, 21-CH, 0.88 (t, J=7.5 Hz, 3H, 25-$CH_3$).

Shorter reaction times result in partially selective reduction. Under the same conditions for Example 9 except stopping the reaction after 24 hours, the 5,6 double bond is >90% reduced and the 22,23 double bond is <50% reduced.

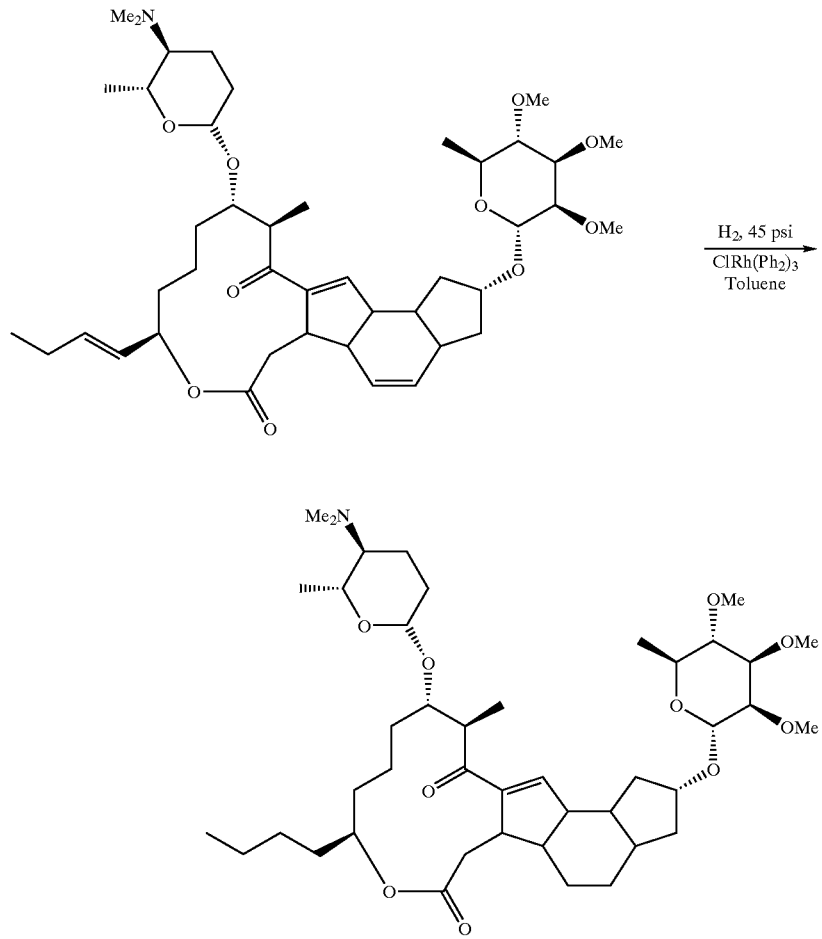

EXAMPLE 12

Synthesis of 22,23-dihydro-for-rham-I (Compound B4) and 5,6,22,23-tetrahydro-for-rham-I (Compound B3)

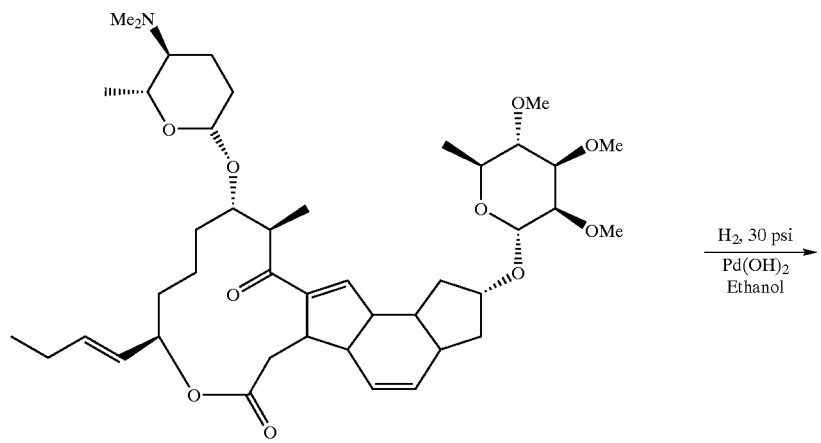

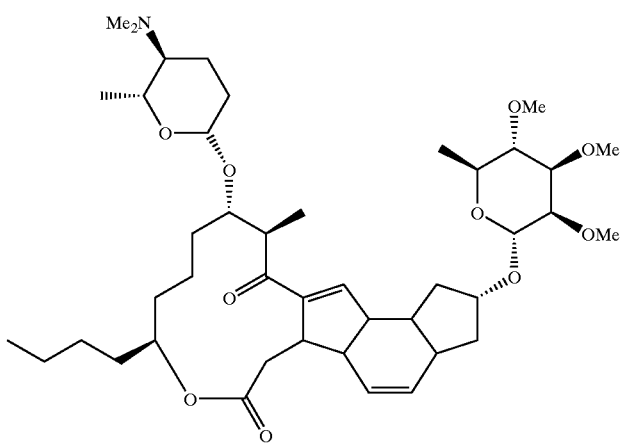

A sample of for-rham-I (Compound 1) (30 mg, 0.04 mmol) was dissolved in 10 mL of EtOH and Pearlman's catalyst (moist Pd(OH)$_2$/C, 10 mg) was added. The solution was hydrogenated at 45 psi for 20 min, then the solution was filtered and concentrated NMR showed a 2:1 mixture of 22,23-dihydro-for-rham-I (Compound B4) and 5,6,22,23-tetrahydro-for-rham-I (Compound B3). For B3, M.S. 763.0 (M+1). NMR δ 6.75 and 6.85 (s, 1H, 13-CH 1:2 ratio, for 5,6,22,23-tetrahydro and 22,23-dihydro, respectively).

Scheme C. Epoxidation of Double Bonds

The double bonds at positions 5,6 and 22,23 can also be oxidized to the corresponding epoxy derivatives by use of any of a variety of oxidizing agents such as m-chloro peroxybenzoic acid. Under these conditions, compounds that contain a tertiary amine group are first oxidized to the corresponding N-oxide. The second molar equivalent of oxidant preferentially forms an epoxide at the 5,6-position, and a third equivalent of oxidant results in bis-epoxidation. The N-oxides can then be reduced to the original amines by reacting the material with an inorganic reducing agent such as sodium bisulfite (Scheme C).

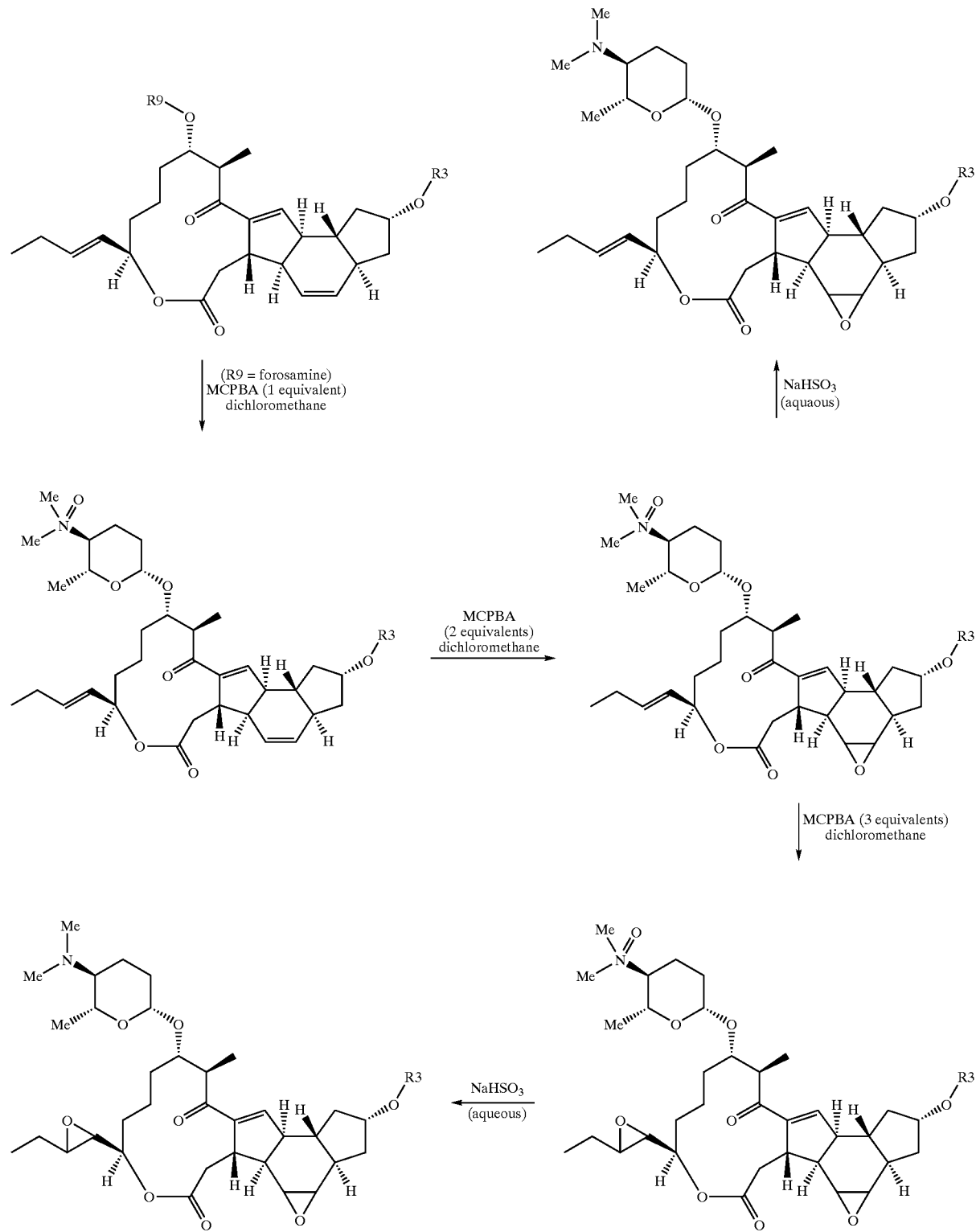

TABLE C
Examples of compounds obtainable using SCHEME C
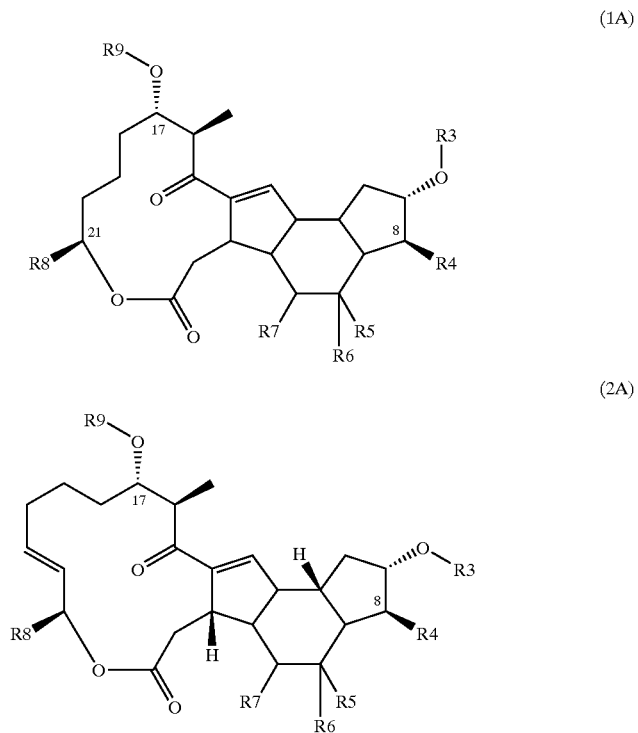
| cmpd no. | SM* | formula | R3 | R5 | R6 | R7 | R8 | R9 |
|---|---|---|---|---|---|---|---|---|
| C1 | 1 | 1A | (3a) | H | -O-(alpha epoxide) | | 1-butenyl | (9a) |
| C2 | 17 | 1A | (3a) | H | -O-(alpha epoxide) | | 1-butenyl | H |
| C3 | 17 | 1A | (3a) | H | -O-(beta epoxide) | | 1-butenyl | H |
| C4 | 17 | 1A | (3a) | H | -O-(beta epoxide) | | H$_3$C–CH–CH$_2$ (epoxide) | H |
| C5 | C6 | 1A | (3a) | H | -O-(beta epoxide) | | H$_3$C–CH–CH$_2$ (epoxide) | (9b) |
| C6 | 1 | 1A | (3a) | H | -O-(beta epoxide) | | 1-butenyl | (9b) |
*SM = starting material

EXAMPLE 13

Synthesis of 5,6-epoxy-for-rham-I (Compound C1)

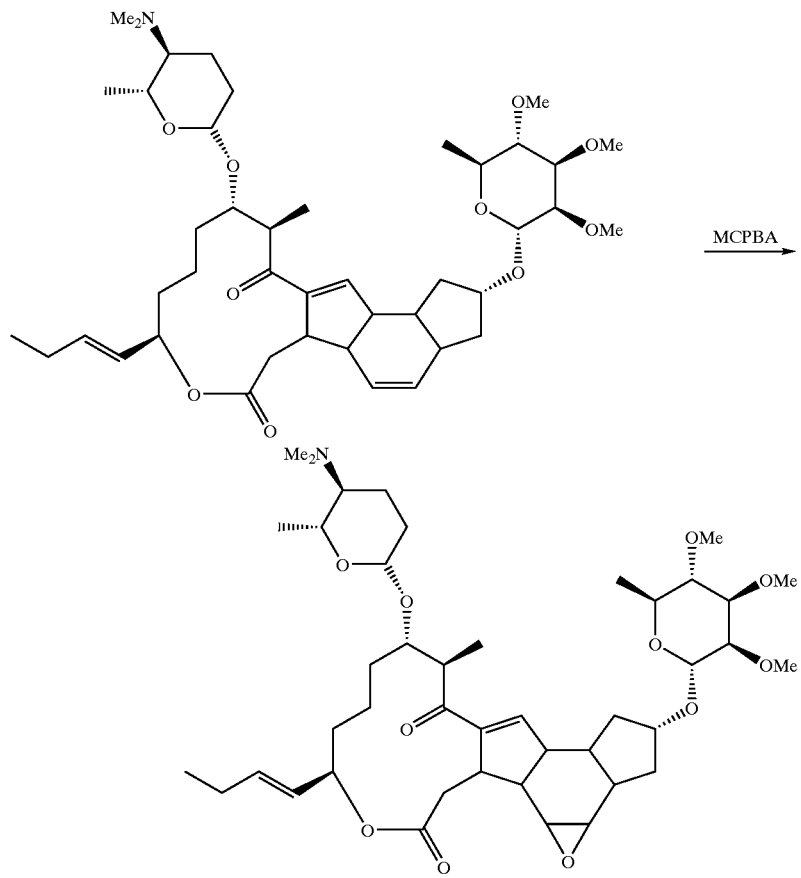

To a solution of for-rham-I (Compound 1) (220 mg, 0.29 mmol) in 5 ml of dichloromethane was added m-chloroperoxybenzoic acid (Aldrich, 50–60%; 167 mg, 0.58 mmol), in portions over 2 h. The solution was allowed to stir at ambient temperature for a total of 3 h, then it was treated with an aqueous solution of $Na_2SO_3$ (75 mg in 2 ml of $H_2O$). This solution was stirred for 3 h, then the layers were separated and the organic phase was dried and concentrated. Chromatography (C-18, 75%–85% MeOH/$H_2O$ gradient) furnished 85 mg of 5,6-α-epoxy for-rham-I (Compound C1) as a white solid foam. M.S. M+1 ion at 774.94, NMR δ 6.60 (s, 1H, 13-CH).

EXAMPLE 14

Synthesis of α-5.6-epoxy rham-I (Compound C2) and 5,6,22,23-bis-epoxy rham-I (Compound C4)

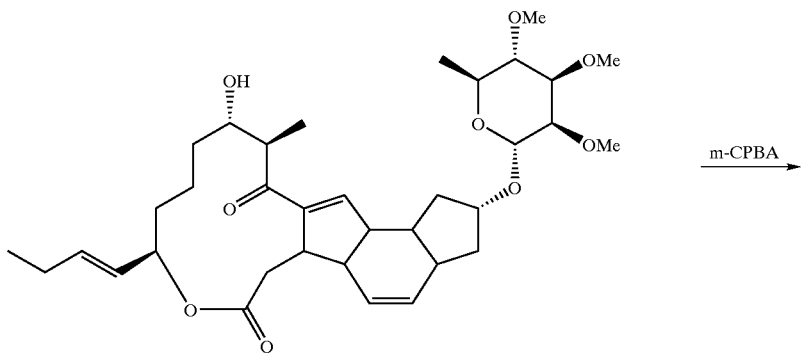

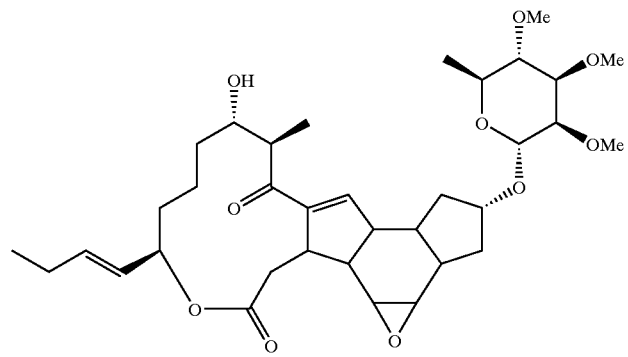

A solution of 170 mg (0.275 mmol) of rham-I (Compound 17) in 5 ml of dichloromethane was sired at ambient temperature under nitrogen while MCPBA (90 mg of 55–60%, 0.29 mmol) was added in portions over 5 min. Stirring was continued for 18 h, then the solution was diluted with 10 ml of dichloromethane and washed with 10 ml of saturated NaHCO3 solution. The organic layer was dried and concentrated to yield a foam, which was chromatographed (C-18, 80:20 MeOH:H2O) to give α-5,6-epoxy rham-I (Compound C2) (70 mg), M.S. M+1 ion at 632.94, NMR δ 6.60 (s, 1H, 13-CH, β-5,6-epoxy rham-I (15 mg), M.S. M+1 ion at 632.46, NMR δ 6.72 (s, 1H, 13-CH); and 5,6,22,23-bis-epoxy rham-I (Compound C4), M.S. M+1 ion at 649.40.

Scheme D. N-Dealkylation and Realkylation of the Forosamine Group

Any of the compounds in Table 1 that contain a C-17 forosaminyl group can be converted selectively to the corresponding N-desmethyl derivative by treatment with a demethylating reagent such as iodine and sodium acetate, or N-bromosuccinimide, or F-TEDA. These N-monomethyl derivatives can then be realkylated by use of an alkylating agent such as bromopropane and a hindered amine base such as triethylamine or diisopropylethylamine (Hunig's base). Furthermore, the N-monoalkyl derivatives can be transformed into N-cyclicalkyl derivatives, by treatment with a dihaloalkyl compound such as 1,4-diiodobutane and a hindered base in a high boiling solvent such as xylenes. Under these conditions, heating of the intermediate quaternary salt results in expulsion of iodomethane and generation of the neutral N-cyclicalkyl product.

SCHEME D.

-continued

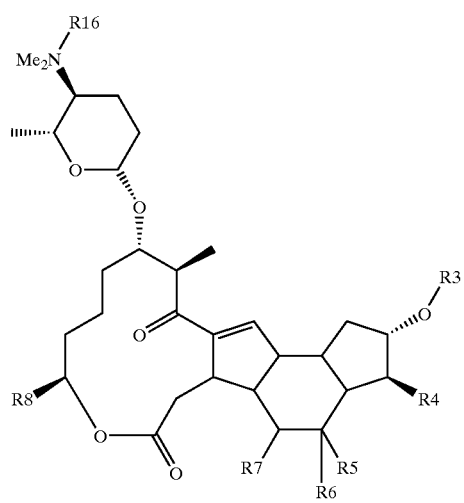 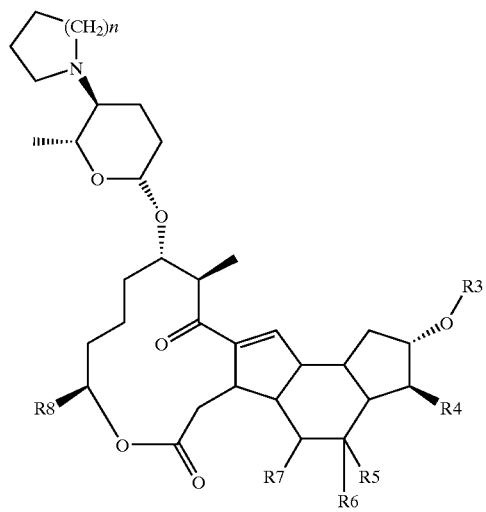

TABLE D

Examples of compounds obtainable using SCHEME D

| Cmpd. No. | SM* | formula | $R^3$ | $R^4$ | $R^5$ | $R^6$ | $R^7$ | $R^8$ | $R^9$ |
|---|---|---|---|---|---|---|---|---|---|
| 3 | 1 | 1A | (3a) | H | H | | Double bond | 1-butenyl | MeNH-tetrahydropyran with Me groups (9c) |
| D1 | 3 | 1A | (3a) | H | H | | Double bond | 1-butenyl | N(Me)(C$_2$H$_5$)-tetrahydropyran with Me groups |
| D2 | 3 | 1A | (3a) | H | H | | Double bond | 1-butenyl | N(Me)(n-C$_3$H$_7$)-tetrahydropyran with Me groups |
| D3 | D6 | 1A | (3a) | H | H | H | H | n-Bu | pyrrolidinyl-tetrahydropyran with Me groups |
| D4 | 3 | 1A | (3a) | H | H | | Double bond | 1-butenyl | N(Me)(CHO)-tetrahydropyran with Me groups |

TABLE D-continued

Examples of compounds obtainable using SCHEME D

| Cmpd. No. | SM* | formula | $R^3$ | $R^4$ | $R^5$ | $R^6$ | $R^7$ $R^8$ | $R^9$ |
|---|---|---|---|---|---|---|---|---|
| D5 | 3 | 1A | (3a) | H | H | Double bond | 1-butenyl | ![structure] |
| D6 | B4 | 1A | (3a) | H | H | Double bond | n-Bu | (9c) |

EXAMPLE 15

Synthesis of N-desmethyl-for-rham-I (Compound 3)

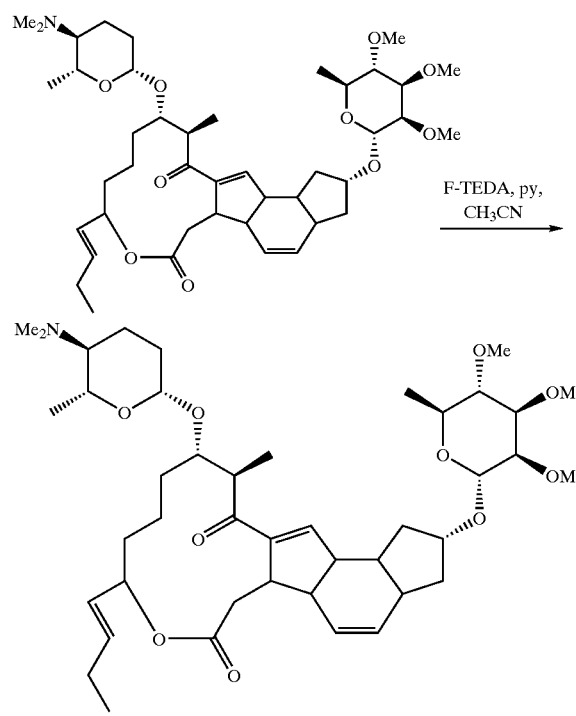

EXAMPLE 16

Synthesis of (N-propyl)-for-rham-I (Compound D2)

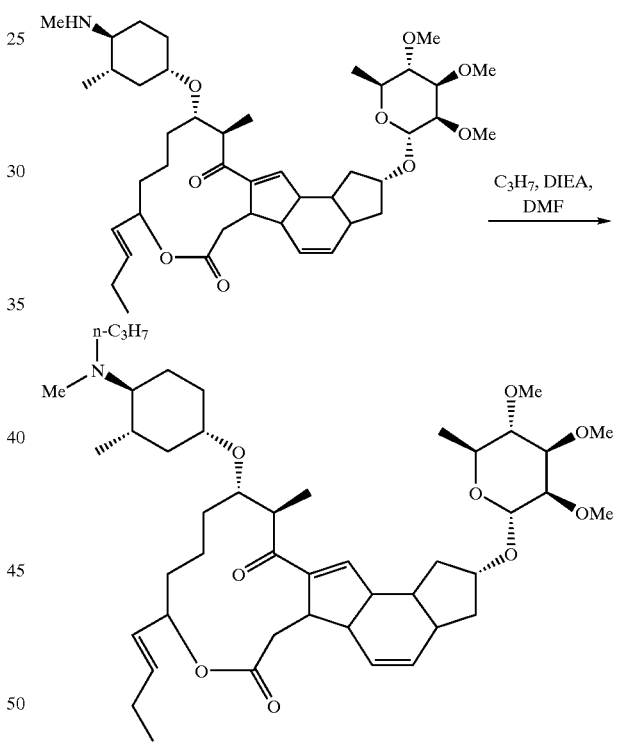

To a solution of for-rham-I (160 mg, 0.211 mmol) in 1.06 ml of acetonitrile was added 0.055 ml of pyridine. The reaction mixture was cooled to 0° at which time 112 mg of F-TEDA was added in 4 equal portions over 0.75 h. After 1.5 h, tlc indicated the reaction was complete. The solution was diluted with 15 ml of ethyl acetate and washed twice with 15 ml of saturated $NaHCO_3$ solution. The organic layer was dried, concentrated, and chromatographed (silica gel), eluting with a $CHCl_3$—MeOH gradient (7–10%). The product-containing fractions were combined and concentrated to give 155 mg of (N-desmethyl)-for-rham-I. M.S. M+1 ion at 744.3, NMR δ 2.4 (s, 3H, NMe).

To a solution of (N-desmethyl)-for-rham-I (29.5 mg, 0.040 mmol) in 1.0 ml of DMF was added 0.008 ml of 1-iodopropane and 0.021 ml DIEA. After 24 h, tlc indicated the reaction was complete. To the solution was added 0.1 ml 1M sodium bisulfite. The reaction mixture was diluted with 10 ml of ether and washed with 10 ml of saturated NaCl solution. The organic layer was dried, concentrated, and chromatographed (silica gel), eluting with 5% $CHCl_3$—MeOH. The product-containing fractions were combined and concentrated to give 9 mg of (N-propyl)-for-rham-L M.S. M+1 ion at 786.4.

EXAMPLE 17

Synthesis of (N-formyl)-for-rham-I (Compound D4)

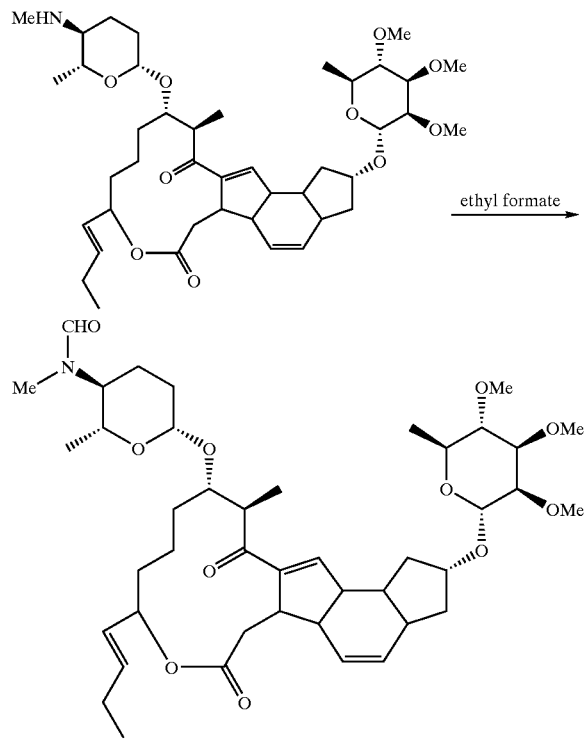

A solution of (N-methyl)-for-rham-I (20 mg, 0.027 mmol) in 2 ml of ethyl formate was heated to reflux. After 1 h, tlc indicated the reaction was complete. The solution was concentrated then diluted with 5 ml of dichloromethane and washed with 5 ml of saturated NaHCO3 solution. The organic layer was dried and concentrated to give 18.0 mg of (N-formyl)-for-rham-I. M.S. M+1 ion at 772, NMR δ 8.12 (s, 1H CHO).

Scheme E. Oxidation Products of Hydroxyl Butenyl Spinosyns

Spinosyn derivatives having a secondary —OH group can be converted into the corresponding ketone by reaction with an oxidant such as N-chlorosuccinimide/diethyl sulfide (Corey-Kim oxidation conditions). The ketone derivatives are insecticidal

SCHEME E

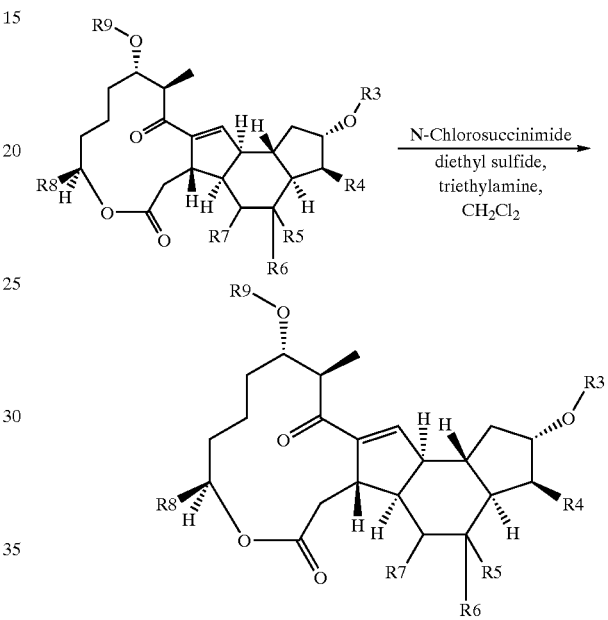

TABLE E

Compounds obtainable using SCHEME E

| cmpd. no. | SM* | formula | R3 | R4 | R5 | R6 | R7 | R8 | R9 |
|---|---|---|---|---|---|---|---|---|---|
| E1 | 5 | 1A | ![](Me, OMe, OMe, O, =O) | H | H | Double bond | 1-butenyl | | (9a) |
| E2 | 6 | 1A | ![](Me, OMe, O, =O, OMe) | H | H | Double bond | 1-butenyl | | (9a) |
| E3 | 8 | 1A | (3a) | | =O | H | Double bond | 1-butenyl | (9a) |
| E4 | 9 | 1A | (3a) | | H | H | Double bond | 3-oxo-1-butenyl | (9a) |

TABLE E-continued

Compounds obtainable using SCHEME E

| cmpd. no. | SM* | formula | R3 | R4 | R5 | R6 | R7 | R8 | R9 |
|---|---|---|---|---|---|---|---|---|---|
| E5 | 12 | 1A | (3a) | | H | H | Double bond | 1-butenyl | ![pyranone with Me and O] |
| E6 | 32 | 1A | ![pyranone with Me, OMe, OMe] | | H | H | Double bond | 1-butenyl | (9a) |
| E7 | B17 | 1A | (3a) | | H | H | H | H | 3-oxo-1-butyl | (9a) |

EXAMPLE 18

Synthesis of for-(3'-ketorham)-I (Compound E2)

Ethyl side (0.11 mL, 0.99 mmol) was added dropwise by syringe during 2–3 min to a cold (−78° C.) well-stirred, nitrogen blanketed suspension of N-chlorosuccinimide (0.12 g, 0.90 mmol) in dichloromethane and the mixture was stirred at −78° C. for 0.5 h. For-3'-(O-desmethylrham)-I (0.20 g, 0.26 mmol) in 2 mL of dichloromethane was added dropwise to the resulting solution during 5 min while keeping the reaction temperature below −60° C. and this solution then stirred at −78° C. for 6 h. Triethylamine (0.125 mL, 0.90 mmol) was then added drop-wise during 2–3 min and the solution then allowed to warm to ambient temperature. The reaction mixture was then diluted with dichloromethane (10 mL) and washed successively with 0.1 N aq. HCl (2×10 mL), sat. NaHCO$_3$ (10 mL) and brine (10 mL) and finally dried (Na$_2$SO$_4$). Concentration left 0.32 g of for-(3'-ketorham)-I as a thick, pale yellow oil: $^1$HNMR (CDCl$_3$, 600 MHz) □ 5.02 (d, J=1.7H, 1H, H-1'), 3.58 (d, J=1.7 Hz, 1H, H-2').

Scheme F. Removal of tri-O-methylrhamnosyl Group and Replacement with Other Sugars The rhamnosyl sugar of butenyl spinosyn can be replaced by other sugars. This involves oxidation of the 3'-OH group to the 3'-keto (Scheme E) and base-catalyzed elimination to form the C9-pseudoaglycone (Scheme F). The C9-pseudoaglycone is then treated with an activated glycosyl unit to generate the new C9-sugar derivative.

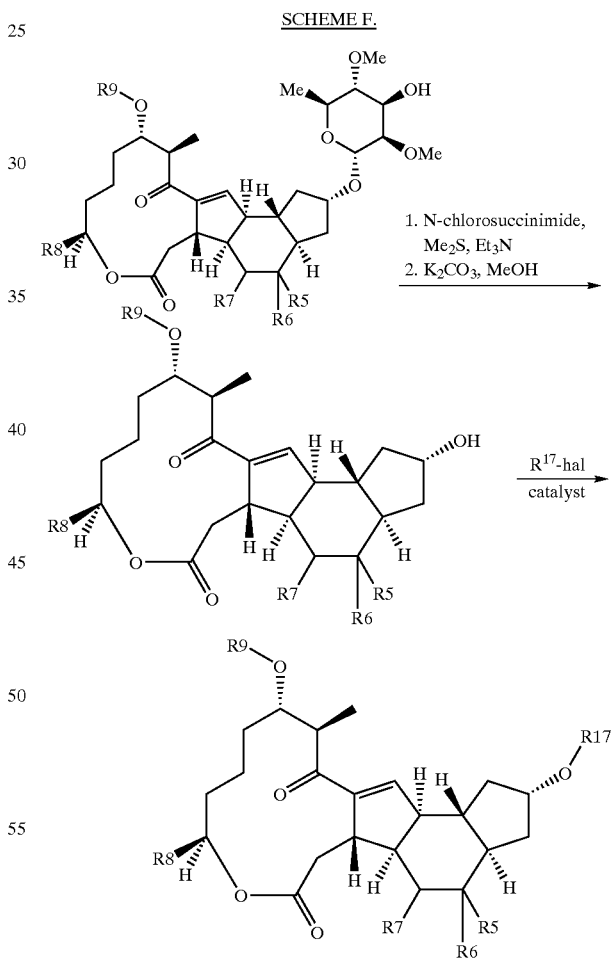

SCHEME F.

TABLE F

Examples of compounds obtainable using SCHEME F.

| Cmpd. No. | SM* | formula | R¹⁷ | R³ | R⁶ | R⁷ | R⁸ | R⁹ |
|---|---|---|---|---|---|---|---|---|
| F1 | 6 | 1A | (MeO, OMe, OMe, OMe pyranose structure) | H | Double bond | 1-butenyl | (9a) |
| F2 | 6 | 1A | (Me, OMe, OMe pyranose structure) | H | Double bond | 1-butenyl | (9a) |
| F3 | 6 | 1A | (Me, OMe, N₃ pyranose structure) | H | Double bond | 1-butenyl | (9a) |
| F4 | 6 | 1A | (Me, OEt, OEt, OEt pyranose structure) | H | Double bond | 1-butenyl | (9a) |
| F5 | 6 | 1A | (Me, OEt, OEt pyranose structure) | H | Double bond | 1-butenyl | (9a) |

*SM = starting material

EXAMPLE 19

Synthesis of for-I (21-butenyl-spinosyn A 9-Psa) (Intermediate)

Anhydrous $K_2CO_3$ (0.41 g, 3.00 mmol) was added in one portion to a solution of all of for-3'-ketorham)-I (0.32 g, 0.26 mmol as 100%) in MeOH (10 mL) and this suspension was stirred for 3 h at ambient temperature. The mixture was then diluted with water (2.5 mL), cooled to 0–5° C. and neutralized by the drop-wise addition during 2–3 min of 3.0 mL 2N HCl. The mixture was then concentrated at reduced pressure at 25° C. to approx. ⅓ its volume. Water (5 mL) was then added and the product extracted with dichloromethane (2×10 mL). The organic extracts were then washed successively with sat. $NaHCO_3$ (5 mL) and brine (5 ml) and dried ($Na_2SO_4$). Concentration left 0.22 g of crude 9-pseudoaglycone which was purified by silica gel chromatography with 5% MeOH in $CH_2Cl_2$ as eluent to give 65.0 mg of pseudoaglycone as a colorless foam: ¹HNMR ($CDCl_3$, 600 MHz) δ 4.45 (m, 2H, H-1", H-9); MS 570.4 (M+1).

EXAMPLE 20

Synthesis of for-(6'-methoxyrham)-I and for-(6'-methoxy-β-rham)-I (Compound F1)

To a cold (0° C.), well stirred solution of for-I (65.0 mg, 0.11 mmol) and pyridinium p-toluenesulfonate (41.0 mg, 0.16 mmol) in dry $CH_2Cl_2$ (10 mL) containing powdered 4A molecular sieves (0.20 g), a solution of O-(2,3,4,6-tetra-O-methyl-α-L-mannopyranosyl)trichloroacetimidate (prepared as disclosed in U.S. Pat. No. 6,001,981) (0.3 g, 0.79 mmol) in $CH_2Cl_2$ (3 mL) was added dropwise during 10 min. The cooling bath was removed after 1 h and the reaction mixture let stir at ambient temperature for 5 d. The mixture was then filtered through Celite, the Celite washed with $CH_2Cl_2$ (10 mL) and the combined filtrate and wash washed with sat. $Na_2CO_3$ (2×5 ml) and brine (5 mL) and dried ($MgSO_4$). Concentration left 0.35 g of residue which was flash chromatographed over silica (50 mL) using 3% MeOH in $CH_2Cl_2$ as eluent to yield 38 mg of a 2:1 mixture of for-(6'-methoxyrham)-I and for-(6'-methoxy-β-rham)-I as a colorless foam. This mixture was separated by hplc in one portion over a preparative (25 cm (I)×30 mm (i.d.) reverse phase YMC-ODS-AQ-363-10P column using 85% MeOH and 15% 10 mM (aq.) NH$_4$OAc as the eluent system. The β-anomer elutes first. For-(6'-methoxyrham)-I: colorless foam;($^1$HNMR (CDCl$_3$, 600 MHz) δ 4.94 (s, 1H, H-1'), 4.50 (m, 1H, H-1"). For-(6'-methoxy-p-rham)-I: colorless foam; $^1$HNMR (CDCl$_3$, 600 MHz) δ 4.42 (s, 1H, H-1).

Scheme G. Claisen Type Rearrangements of 24-hydroxy-butenyl Spinosyns

The allylic alcohol in the side chain of the 24-hydroxy-butenyl spinosyns readily undergoes Claisen te rearrangements when treated with N,N-dialkylacetamide dialkylacetals or trialkyl orthoacetates under the proper conditions.

SCHEME G.

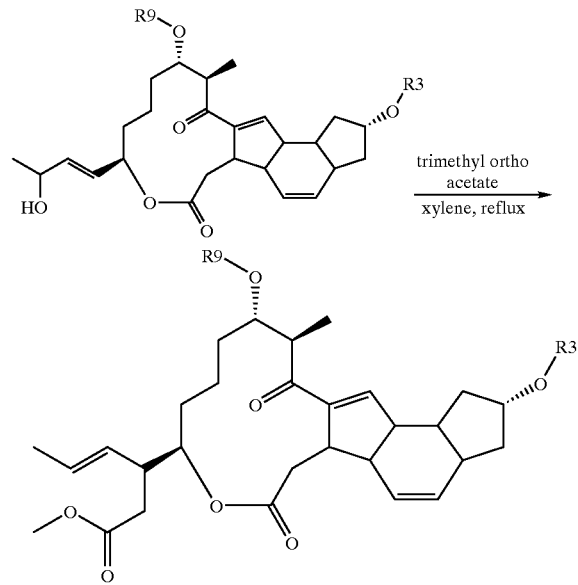

EXAMPLE 21

Synthesis of (Compound G1)

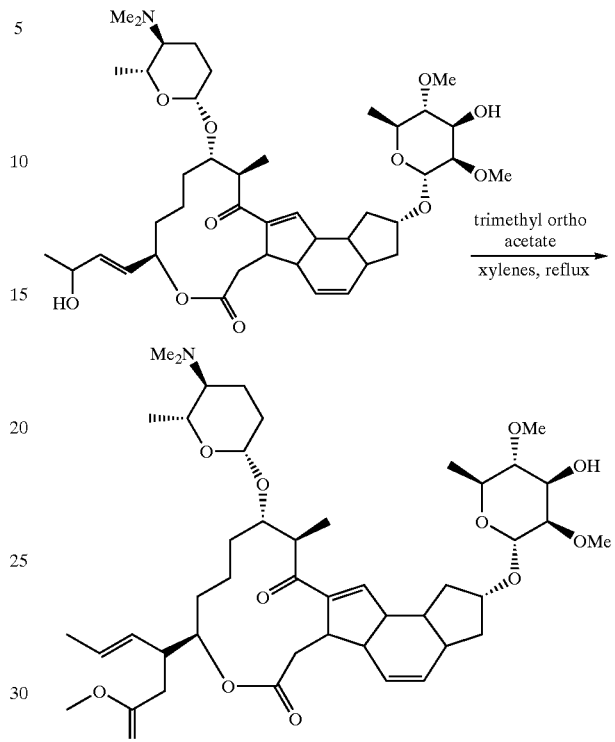

To a solution of 24-hydroxy-for-(3'-O-desmethyl-rham)-I (Compound 45) (50 mg, 0.07 mmol) in xylenes (0.26 mL) was added trimethyl ortho acetate (0.126 mL, 0.987 mmol). The solution was heated to 190° C. (bath temperature) for 1 h. The cooled solution was chromatographed (silica gel), eluting with a CHCl$_3$—MeOH gradient (1–3° h) to give 24 mg of compound G1 as a light tan foam. M.S. M+1 ion at 817.3, NMR δ 5.58–5.02 (m, 2H, 23–24-CH), 3.62 (s, 3H, CO$_2$CH$_3$).

TABLE G

Examples of compounds obtainable using SCHEME G

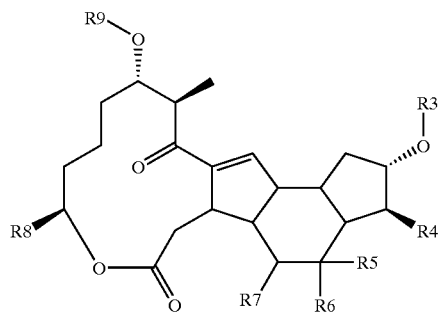

| Cmpd. No. | SM* | formula | R$^3$ | R4 | R$^5$ | R$^6$ | R$^7$ | R$^8$ | | R$^9$ |
|---|---|---|---|---|---|---|---|---|---|---|
| G1 | 45 | 1A | (3c) | H | H | Double bond | | CH$_3$CH=CHCH(CH$_2$CO$_2$Me)- | | (9a) |
| G2 | 45 | 1A | (3c) | H | H | Double bond | | CH$_3$CH=CHCH(CH$_2$C(O)NMe$_2$)- | | (9a) |

*SM = starting material

EXAMPLE 22

Synthesis of Compound G2

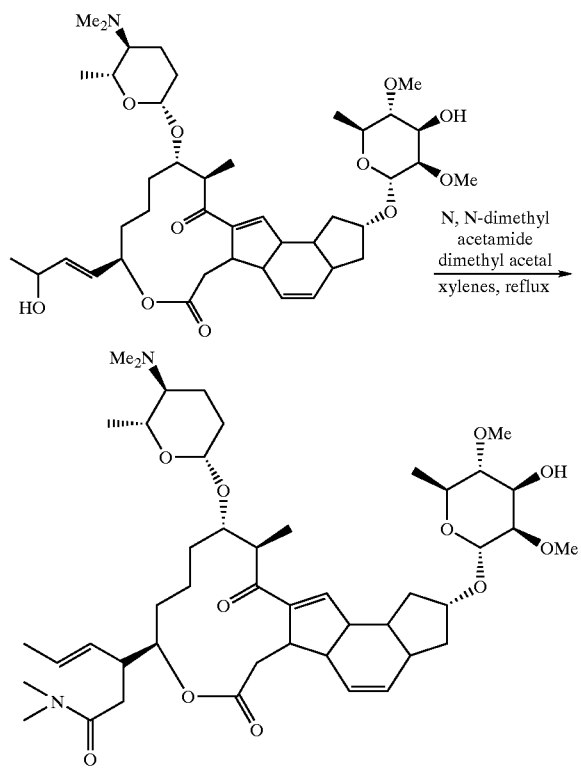

To a solution of 24-hydroxy-for-(3'-desmethyl-rham)-I (Compound 45) (25 mg, 0.033 mmol) in xylenes (0.131 mL) was added N,N-dimethyl acetamide dimethyl acetal (0.020 mL, 0.13 mmol). The solution was heated to 145° C. (bath temperature) for 10 m. The cooled solution was chromatographed (silica gel), eluting with a $CHCl_3$—MeOH gradient (1–5%) to give 19 mg of compound G2 as a white powder. M.S. M+1 ion at 830.4, NMR δ 5.55–5.25 (m, 2H, 23–24° C., 2.96 (s, 3H $NCH_3$), 2.90 (s, 3H $NCH_3$).

The compounds claimed herein include all isomers and any acid addition salts of the compounds and their isomers.

The compounds claimed herein exist in several diastereomeric isomers. Because there are multiple stereogenic centers, it is anticipated that the diasteromeric isomers will have utility as insecticides. Although some diastereomeric isomers may be more efficacious than others, all the diastereomeric isomers are equivalent to the claimed invention.

The acid addition salts of the compounds disclosed herein, where possible, are also useful in producing agricultural products. These salts are useful for example, in separating and purifying the Formula (1A) compounds. In addition, some of these salts may have increased water-solubility. Acid addition salts may be prepared from the compounds disclosed in Formula (1A) where $R^9$ is a basic nitrogen-containing sugar molecule such as forosamine. The salts of the compounds are prepared using standard technology for preparing salts which are well known to those skilled in the art. Acid addition salts that are particularly useful include, but are not limited to, salts formed by standard reactions with both organic and inorganic acids such as sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

Insecticide and Miticide Activity

Compounds of Formula (1B) and (2B) (i.e. compounds of Formula (1A) and (2A) compounds where $R^9$ is a sugar moiety) are useful for the control of insects and mites. Therefore, a further aspect of the present invention is directed to methods for inhibiting an insect or mite which comprises applying to the locus of the insect or mite an insect- or mite-inhibiting amount of a Formula (1B) or (2B) compound.

The "locus" of the insect or mite refers to the environment in which the insect or mite lives or where its eggs ae present, including the air surrounding it, the for it eats, or objects which it contacts. For example, plant-ingesting insects or mites can be controlled by applying the active compound to plant parts which the insects or mites eat or habit, particularly the foliage.

By the term "inhibiting an insect or mite" it is meant that there is a decrease in the number of living insects or mites or a decrease in the number of eggs. The extent of reduction accomplished by a compound depends, of course, on the application rate of the compound, the particular compound used, and the target insect or mite species. At least an insect-inactivating or mite-inactivating amount should be used. By "inactivating amount" it is meant that an amount of compound is used to cause measurable reduction in the treated insect or mite population. Typically from about 1 to about 1,000 ppm (or 0.01 to 1 Kg/acre) of compound is used.

The compounds show activity against a number of insects and mites. More specifically, the compounds show activity against members of the insect order Lepidoptera such as the beet armyworm, tobacco budworm, codling moth and cabbage looper. Other typical members of this order include the southern armyworm, cutworms, clothes moths, Indian meal moth, leaf rollers, corn earworm, cotton bollworm, European corn borer, imported cabbage worm, pink bollworm bagworms, Eastern tent caterpillar, sod webworm, and full armyworm.

The compounds also show activity against members of the order Coleoptera (the beetles and weevils such as the Colorado potato beetle, spotted and striped cucumber beetles, Japanese beetle, and boll weevil) and *Diptera* (the true flies such as the house fly, mosquitoes, fruit flies, stable and horn flies, and leaf miners).

The compounds also show activity against members of the order Hempitera (true bugs such as plant bugs, stink bugs, and chinch bugs), *Homoptera* (such as the aphids, leafhoppers, planthoppers, whiteflies, scales, and mealybugs), *Thysanoptera* (thrips), *Orthoptera* (such as cockroaches, grasshoppers, and crickets), *Siphonaptera* (fleas), *Isoptera* (termites), and members of the *Hymenoptera* order Formicidae (ants).

The compounds also show activity against the two-spotted spider mite, which is a member of the *Arachnid* order Acarina. Other typical members of this order include plant parasites such as the citrus red mite, European red mite, and citrus flat mite, and animal parasites such as the mange mite, scab mite, sheep scab mite, chicken mite, scalyleg mite, depluming mite and dog follicle mite.

Specific representative anthropod pests which can be controlled by the present compounds include the following: *Amblyomma americanum* (Lone-star tick), *Amblyomma*

*maculatum* (Gulf Coast tick), *Argas persicus* (fowl tick), *Boophilus microplus* (cattle tick), *Chorioptes* spp. (mange mite), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick), *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus* (brown dog tick), *Sarcoptes scabiei* (mange mite), *Aedes* (mosquitoes), *Anopheles* (mosquitoes), *Culex* (mosquitoes), *Culiseta, Bovicola bovis* (cattle biting louse), *Callitroga homnivorax* (blowfly), *Chrysops* spp. (deer fly), *Cimex lectularius* (bed bug), *Cochliomyia* spp. (screwworm), *Ctenocephalides canis* (dog flea), *Ctenocephalides felis* (cat flea), *Culicoides* spp. (midges, sandflies, punkies, or no-see-ums), *Damalinia ovis* (sheep biting louse), *Dermatobia* spp. (warble fly), *Gasterophilus haemorrhoidalis* (nose bot fly), *Gasterophilus intesinalis* (common horse bot fly), *Gasterophilus nasalis* (chin fly), *Glossina* spp. (tsetse fly), *Haematobia irritans* (horn fly, buffalo fly), *Haematopinus asini* (horse sucking louse), *Haematopinus eurystemus* (short nosed cattle louse), *Haematopinus ovillus* (body louse), *Haematopinus suis* (hog louse), *Hydrotaea irritans* (head fly), *Hypoderma bovis* (bomb fly), *Hypoderma lineatum* (heel fly), *Linognahus ovillus* (body louse), *Linognathus pedalis* (foot louse), *Linognathus vituli* (long nosed cattle louse), *Lucilia* spp. (maggot fly), *Melophagus ovinus* (sheep ked), *Musca* spp. (house fly, face fly), *Oestrus ovis* (nose bot fly), *Pediculus* spp. (lice), *Phlebotomus* spp. (sandfly), *Phormia regina* (blowfly), *Psorophora* spp. (mosquito), *Pthirus* spp. (lice), *Reduvius* spp. (assassin bug), *Simulium* spp. (black fly), *Solenopotes capillatus* (little blue cattle louse), *Stomoxys calcitrans* (stable fly), *Tabanus* spp. (horse fly), *Tenebrio* spp. (mealworms), *Triatoma* spp. (kissing bugs).

In one preferred embodiment, the present invention is directed to a method for inhibiting a susceptible insect of the order *Lepidoptera* that comprises applying to a plant an effective insect-inactivating amount of a Formula (1B) or (2B) compound in accordance with the present invention. Another preferred embodiment of the invention is directed to a method of inhibiting biting flies of the order Diptera in animals which comprises administering an effective pest-inhibiting amount of a Formula (1B) or (2B) compound orally, parenterally, or topically to the animal. Another preferred embodiment of the invention is directed to a method of inhibiting mites of the order Acarina which comprises applying to the locus of the mite a mite-inactivating amount of a Formula (1B) or (2B) compound.

Insect Screens

A Tobacco Budworm (*Heliothis Virescens*) Feeding Assay

To compare insecticidal activities of compounds of the invention against second instar larval *Heliothis virescens* leaf-dip bioassay was used. Cotton cotyledon leaves were dipped in a test solution made up of the compound dissolved in acetone: Millipore water (2:1) at rates of 400 ppm to 1.56 ppm. Each cotyledon was placed individually on top of a moistened (distilled water) cotton ball in the bottom of a 1 oz plastic cup and allowed to dry (one hour). After drying, a single laboratory-reared second instar *Heliothis virescens* larva (mean weight 15 mg.) was placed on the treated leaf and the cup sealed with a lid, and held at 27° C. for four days. Percent mortality was determined at the end of the holding period. Results are presented in Table 2.

B. Tobacco Budworm (*Heliothis virescens*) Topical Assay

An additional measure of the relative insecticidal activities of the compounds of the invention was generated by using a 1 ug/ul acetone solution of each compound applied at 1 ug/larva of laboratory-reared *Heliothis virescens* larvae (mean weight of 22 mg). Each compound was applied along the dorsum of each of six larvae. Treated larvae were then held for two days at 21° C., 60% RH in six-well plastic culture plates. Larvae were each supplied with a 1 cm$^3$ of agar-based lepidoptera diet for sustenance during the two-day post-exposure interval. Percent mortality was determined at the end of a two-day period. Results are presented in Table 2.

C. Cotton Aphid (*Aphis gossypii*) Assay

Insecticidal activities of the compounds of the invention were also evaluated against cotton aphids (*Aphis gossyppi*) as follows. Summer crookneck squash seedlings at the expanded cotyledon stage are primed to a single cotyledon and infested with cotton aphids 16–24 hours before application of the test material by transfer of infested foliage cut from a stock colony. Immediately prior to spray application of the test material, the transfer foliage is removed from the squash plants. The test material is dissolved at 1 mg/ml in 90:10 acetone:alcohol, then diluted in water containing 0.05% Tween 20 (polyethylene (20) sorbitan monolaurate) to give test solution at a concentration of 50 ppm. The plants were sprayed with the test solution using an atomizing sprayer at 17 psi. Both surfaces of the cotyledons are covered until runnoff, and then allowed to dry. Activity of the compound was determined at three days after treatment. Activity was rated as a percent based on the number of aphids present in plants sprayed with solvent only.

TABLE 2

Activity of spinosyns against *Heliothis virescens* (Tobacco Budworm) Feeding and Topical Bioassays and *Aphis gossypii* (Cotton Aphid) Bioassay

| Compound | Mass Spec. parent (or M + 1) peak | Tobacco Budworm Feeding (96 h) Rate (ppm) | Tobacco Budworm Feeding (96 h) Mortality (%) | Tobacco Budworm Typical (48 h) Rate (□g/larva) | Tobacco Budworm Typical (48 h) Mortality (%) | Cotton Aphid mortality (72 h) Rate (ppm) | Cotton Aphid mortality (72 h) Mortality (%) |
|---|---|---|---|---|---|---|---|
| A1 | 772.5 | 1.56 | 100 | | | 50 | 87 |
| A2 | 772.5 | 1.56 | 100 | 1 | 100 | 50 | 97 |
| A3 | | | | 1 | 67 | | |
| A4 | | 400 | 100 | | | 50 | 99 |
| A5 | 790.5 | 400 | 100 | | | 50 | 53 |
| A6 | 786.5 | | | 1 | 100 | 50 | 54 |
| A14 | 748.4 | | | 1 | 83 | 50 | 92 |
| A15 | 777.4 | 6.25 | 100 | | | 50 | 100 |
| A16 | 790.4 | 6.25 | 100 | | | 50 | 100 |
| A17 | 804.4 | 6.25 | 10 | 1 | 100 | 50 | 100 |
| A18 | 818.3 | 1.56 | 20 | 1 | 33 | 50 | 91 |
| A19 | 816.4 | 400 | 100 | | | 50 | 99 |
| A20 | 844.4 | 400 | 100 | | | 50 | 99 |
| A21 | 873.4 | 400 | 100 | | | 50 | 59 |
| A22 | 774.4 | 400 | 100 | | | 50 | 99 |
| A23 | 788.4 | 400 | 100 | | | 50 | 100 |
| A24 | 802.4 | 400 | 100 | | | 50 | 99 |

TABLE 2-continued

Activity of spinosyns against *Heliothis virescens* (Tobacco Budworm) Feeding and Topical Bioassays and *Aphis gossypii* (Cotton Aphid) Bioassay

| Compound | Mass Spec. parent (or M + 1) peak | Tobacco Budworm Feeding (96 h) Rate (ppm) | Mortality (%) | Tobacco Budworm Typical (48 h) Rate (□g/larva) | tality (%) | Cotton Aphid mortality (72 h) Rate (ppm) | Mortality (%) |
|---|---|---|---|---|---|---|---|
| A25 | 806.2 | | | 1 | 83 | 50 | 79 |
| A26 | 747.4 | | | 1 | 83 | 50 | 89 |
| A27 | 845.4 | | | 1 | 100 | 50 | 33 |
| A28 | 858 | 400 | 100 | | | 50 | 48 |
| B2 | 790.7 | | | 1 | 83 | 50 | 97 |
| B3 | 763.02 | 6.25 | 100 | 1 | 100 | 50 | 53 |
| B3/B4, 2:1 | 763.02 | 1.56 | 100 | | | 50 | 98 |
| B3/B7, 1:1 | | | | | | 50 | 97 |
| B5 | 776.4 | | | | | 50 | 96 |
| B6 | 778.5 | | | 1 | 100 | 50 | 94 |
| B11 | 746.3 | | | | | | |
| B12 | 748.4 | 600 | 100 | | | | |
| B13 | | | | | | | |
| B14 | | | | | | | |
| B15 | | | | | | | |
| B16 | 776.3 | | | | | | |
| B17 | 778.3 | | | 1 | 17 | 50 | 11 |
| C1 | 774.9 | 400 | 100 | | | 50 | 95 |
| D1 | 772.5 | | | 1 | 83 | | |
| D2 | 786.4 | | | | | 50 | 50 |
| D4 | 772 | 400 | 100 | | | 50 | 92 |
| D5 | 786.3 | 400 | 100 | | | 50 | 92 |

Industrial Composition

The Formula (1B) or (2B) compounds are applied in the form of compositions, which are also a part of this invention. These compositions comprise an insect- or mite-inactivating amount of a Formula (1B) or (2B) compound in a phytologically acceptable inert carrier. The active component, the Formula (1B) or (2B) compound, may be present as a single Formula (1B) or (2B) compound, a mixture of two or more Formula (1B) or (2B) compounds or a mixture of any of the Formula (1B) or (2B) compounds together with the dried portion of the fermentation medium in which it is produced.

Compositions are prepared according to the procedures and formula which are conventional in the agricultural or pest control art, but which are novel and important because of the presence of one or more of the compounds of this invention. The compositions may be concentrated formulations, which are dispersed in water or may be in the form of a dust, bait or granular formulation used without further treatment.

The dispersions in which the compounds or crude dried material are applied are typically aqueous suspensions or emulsions prepared from concentrated formulations of the compounds or crude material. The water-soluble or water-suspension or emulsifiable formulations are either solids, wettable powders, or liquids, known as emulsifiable concentrates or aqueous ons. Wettable powders may be agglomerated or compacted to form water dispersible granules. These granules comprise mixtures of compound or crude dried material, inert carriers and surfactants. The concentration of the compound or crude dried material is typically between about 0.1% to about 90% by weight. The inert carrier is typically attapulgite clays, montorillonite clays and the diatomaceous earths or purified silicates.

Surfactants comprise typically about 0.5% to about 10% of the wettable powder, where the surfactants are typically sulfonated lignins, condensed napthalene-sulfonates, the napthalene-sulfonates, alkyl-benenesulfonates, alkylsulfonates or nonionic surfactants such as ethylene oxide adducts of alkylphenols or mixtures thereof.

Emulsifiable concentrates of the claimed compounds typically range from about 50 to about 500 grams of compound per liter of liquid, equivalent to about 10% to about 50%, dissolved in an inert carrier which is a mixture of a water immiscible solvent and emulsifiers. Organic solvents include organics such as xylenes, and petroleum fractions such as high-boiling naphthlenic and olefinic portions of petroleum which include heavy and aromatic naphtha. Other organics may also be used such as terpenic solvents-rosin derivatives, aliphatic ketones such as cyclohexanone and complex alcohols. Emulsifiers for emulsifiable concentrates are typically mixed ionic and/or nonionic surfactants such as those mentioned herein or their equivalents.

Aqueous suspensions may be prepared containing water-insoluble compounds of this invention, where the compounds are dispersed in an aqueous vehicle at a concentration typically in the range of between about 5% to about 50% by weight. The suspensions are prepared by finely grinding the compound and vigorously mixing it into a vehicle of water, surfactants, and dispersants as discussed herein. Inert ingredients such as inorganic salts and synthetic or natural gums may also be employed to increase the density and/or viscosity of the aqueous vehicle as is desired.

Precipitated flowables may be prepared by dissolving the active molecule in a water-miscible solvent and surfactants or surface-active polymers. When these formulations are mixed with water, the active compound precipitates with the surfactant controlling the size of the resulting microcrystalline precipitate. The size of the crystal can be controlled through the selection of specific polymer and surfactant mixtures.

The compounds may also be applied as a granular composition that is applied to the soil. The granular composition typically contains from about 0.5% to about 10% by weight of the Formula (1B) or (2B) compound. The compound is dispersed in an inert carrier which is typically clay or an equivalent substance. Generally, granular compositions are prepared by dissolving the compound in a suitable solvent and applying it to a granular carrier which has been pre-formed to the desirable particle size. The particle size is typically between about 0.5 mm to 3 mm. The granular compositions may also be prepared by forming a dough or paste of the carrier and compound, drying the combined mixture, and crushing the dough or paste to the desired particle size.

The compounds may also be combined with an appropriate organic solvent. The organic solvent is typically a bland petroleum oil that is widely used in the agricultural industry. These combinations are typically used as a spray. More typically, the compounds are applied as a dispersion in a liquid carrier, where the liquid carrier is water. The compounds may also be applied in the form of an aerosol composition. The compound is dissolved in an inert carrier, which is a pressure-generating propellant mixture. The aerosol composition is packaged in a container, where the mixture is dispersed through an atomizing valve. Propellant mixtures contain either low-boiling halocarbons, which may be mixed with organic solvents or aqueous suspensions pressurized with inert gases or gaseous hydrocarbons.

The amount of compound applied to the loci of insects and mites is not critical and can easily be determined by those skilled in the art. Generally, concentrations of from about 10 ppm to about 5,000 ppm of Formula (1B) or (2B) compounds provide the desired control. For crops such as soybeans and cotton, the rate of application is about 0.01 to about 1 kg/ha, where the compound is applied in a 5 to 50 gal/A spray formulation. The compounds may be applied to any locus inhabited by an insect or mite. Such locus typically is cotton, soybean and vegetable crops, fruit and nut trees, grape vines, houses and ornamental plants.

The action of the compositions according to the invention can be broadened considerably by adding other, for example insecticidally, acaricidally, and/or nematocidally active, ingredients. For example, one or more of te following compounds can suitably be combined with the compounds of the invention:
organophosphorus compounds such as acephate, azinphosmethyl cadusafos, chlorethoxyfos, chlorpyrifos, coumaphos, dematon, demeton-S-methyl diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion, mevinphos, monocrotophos, parathion, phorate phosalone, phosmet, phosphamidon, phosphocarb, phoxim, profenofos, propaphos, propetamphos, prothiofos, pyrimiphos-methyl, pyrimiphos-ethyl quinalphos, sulprofos; tebupirimphos, temephos, terbufos, tetrachlorvinphos, thiafenox, thiometon, triazophos, and trichlorphon, , carbamates such as aldicarb, bendiocarb, benfuracarb, bensultap, BPMC, butoxycarbocim, carbaryl, carbofuran, carbosulfan cloethocarb, ethiofencarb, fenobucarb, furathiocarb, methiocarb isoprocarb, methomyl, oxamyl, pirimicarb, promecarb, propoxur, thiodicarb, and thiofurox, pyrethroids such as acrinathrin, allethrin, beta-cyfluthrin bifenthrin, bioresmthrin cyfluthrin cyhalothrin; lambda-cyhalothrin; gamma-cyhalothrin cypermethrin; alpha-cypermethrin; zeta-cypermethrin; deltamethrin, esfenvalerate, fenvalerate, fenfluthrin fenpropathrin flucythrinate, flumethrin, fluvalinate, tau-fluvalinate, halfenprox, permethrin, protrifenbute, resmethrin, silafluofen, tefluthrin, tetramethrin, tralometrin fish safe pyrethroids for example ethofenprox, natural pyrethrin, tetramethrin, s-bioallethrin fenfluthrin and prallethrin, acylureas, other types of insect growth regulators and insect hormone analogs such as buprofezin, chromfenozide, chlorfluazuron, diflubenzuron, fenoxycarb, flufenoxuron, halofenozide, hexaflumuron, hydroprene, leufenuron, methoprene, methoxyfenozide, novaluron, pyriproxyfen, teflubenzuron and tebufenozide, N-[3,5-dichloro-2-fluoro-411,1,2,3,3,3-hexafluoropropoxy) phenyl]-N'(2,6-difluorobenzoyl)urea, neonicotnioids and other nicotinics such as acetamiprid, AKD-1022, cartap, TI-1435, clothiamidin, MTI-446, dinotefuran, imidacloprid, nicotine, nitenpyram, thiamethoxam, thiacloprid, macrolides such as avermectins, milbemycins, or spinosyns for example such as abamectin, ivermectin, milbemycin, emamectin benzoate and spinosad, and other insecticidal, acaricidal, mollscicial and nematocidal compounds or actives such as aldrin, amitraz, azadirachtin, azocyclotin, bifenazate, bromopropylate, chlordimeform, chlorfenapyr, chlofentezine, chlorobenzilate, chlordane, cyhexatin, cyromazin, DDT, dicofol, dieldrin, DNOC, endosulfan, ethoxazole, fenazaquin, fenbutatin oxide, fenproximate beta-fenpyroximate, fipronil, fubenzimine, hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodiclofen, sulfur, tebufenpyrad, tetradifon, triazamate, an insect-active extract from a plant; a preparation containing insect-active nematodes, a preparation obtainable from *Bacillus subtilis, Bacillus thuringiensis*, a nuclear polyhedrosis virus or other like organism genetically modified or native, as well as synergists such as piperonyl butoxide, sesamax, safroxan and dodecyl imidazole, and phagostimulants such as cucurbitacin, sugars and Coax.

WO 00/56156 on "Synergistic Insecticide Mixtures" discloses use of certain previously known spinosyn compounds in combination with agonists or antagonists of nicotinic acetylcholine receptors to control animal pests. Particularly preferred examples of such compounds are imidacloprid, acetamiprid, thiamethoxam, nitenpyram, clothiamidin dinotefuran, thiaclopyrid, and the compound

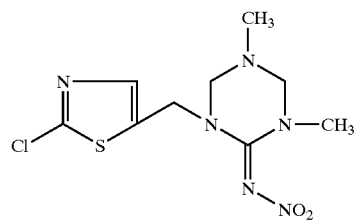

Mixtures of the foregoing agonists and antagonists of nicotinic acetylcholine receptors with the synthetic butenyl-spinosyn compounds of Formulas (1B) and (2B) are similarly useful to control animal pests.

WO 00/35282 on "Combination of Active Ingredients" discloses use of spinosad in combination with A) a fungicidally active compound from the series consisting of benomyl, thiophanate-methyl, acibenzolar, flutolanil, furametpy, fumoxadone, mealaxyl, mefluoxam, azooxystrobin, metominostrobin, capropamide, dicyclocymet, tricyclazole, and oryzemate, and B) an insecticidally active compound from the series consisting of

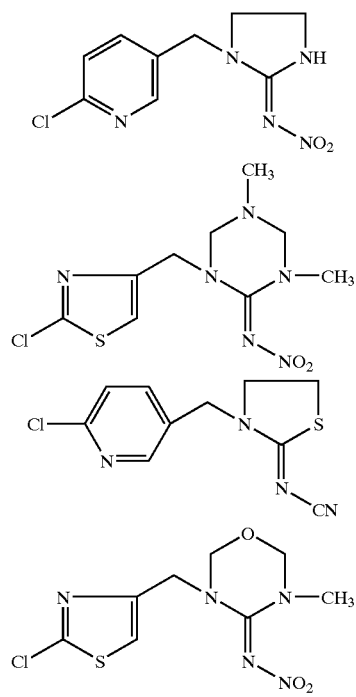

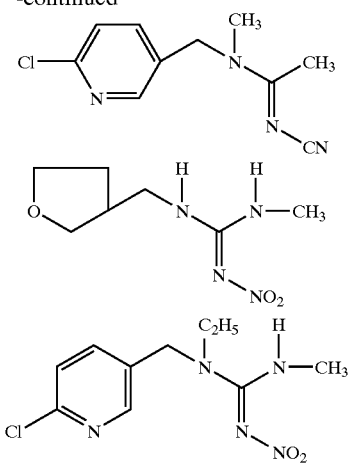

to control insects and fungi. Analogous mixtures in which a synthetic butenyl-spinosyn compound of Formula (1B) or (2B) is substituted for spinosad are similarly useful control insects and fungi.

WO 00/35286 on "Combinations of Active Ingredients" discloses use of a combination of spinosad with A) a compound selected from the group consisting of

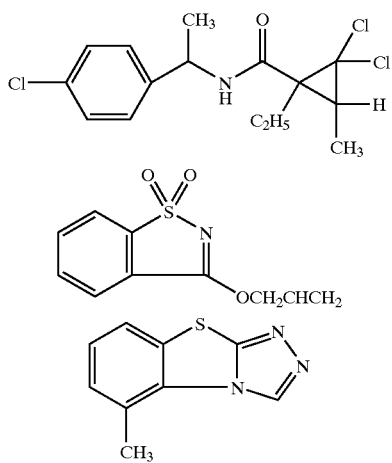

and B) 1-[(6-chloro-3-pyridinyl)-methyl]-N-nitro-2-imidazolidinimine to control animal pests and fungi. Analogous mixtures in which a synthetic butenyl-spinosyn compound of Formula (1B) or (2B) is substituted for spinosad are similarly useful control animal pests and fungi.

WO 99/60856 on "Use of Spinosynes as Soil Insecticides" discloses use of certain previously known spinosyns for treating seeds and for application to plants via the soil or by irrigation to control insects. The synthetic butenyl-spinosyn compounds of Formulas (1B) and (2B) can similarly be used for treating seeds and for application to plants via the soil or by irrigation to control insects.

WO 99/33343 on "Use of Macrolides in Pest Control" discloses use of spinosyns to control pests in transgenic crops, use of spinosyns to protect plant propagation material and plant organs formed at a later time from attack by pests, and use of spinosyns to control wood pests and molluscs. The synthetic butenyl-spinosyn compounds of the present invention can also be used for these purposes.

Animal Health Utility

The compounds of the present invention are also useful for the treatment of animals to control anthropods, i.e.,
insects and arachnids, which are pests on animals. These arthropod pests typically attack their hosts on the external ("ecto") surface; agents which control such pests are referred to as "ectoparasiticides". All animals are subject to attack by such pests, though the problems are most severe among vertebrate hosts. Human beings are potential hosts for many parasites, and in tropical areas and in areas with minimal sanitation, parasitic infections are a regular problem in medical practice. Also highly subject to attack by parasites are the numerous livestock animals, such as cattle, sheep, pigs, goats, buffalo, water buffalo, deer, rabbits, chickens, turkeys, ducks, geese, ostriches, and the like. Horses and other pleasure animals are subject to parasitic attack, as are mink and other animals grown for their fur, and rats, mice and other animals used in laboratory and research settings. Companion animals such as dogs and cats are highly subject to attack by parasites, and because of their close relationship with humans, such parasitism poses problems for the humans with whom they are associated. Fish, crustacea and other aquatic species are also subject to parasitic attack. In short, parasitism involves as hosts essentially the whole range of animals.

The economic toll from ectoparasitic infestations is large. In the livestock realm, animals suffer reduced feed efficiency and growth rates. Milk and wool production suffer, and there is damage to fleece, hides, and pelts. Animals are rendered susceptible to secondary microbiological infections and to further parasite attack. Ectoparasites also cause considerable discomfort even when they are not severely detrimental to health and production.

Although a number of parasiticides are in use, they suffer from a variety of problems, including a limited spectrum of activity, environmental toxicity, the need for repeated treatment, and, in many instances, resistance by ectoparasites. Therefore, there is a continuing need for new ectoparasiticides.

The compounds of Formula (1B) and (2B) provide a new tool in the armamentarium for controlling ectoparasites. In this embodiment, the present invention is directed to a method for inhibiting or killing an arthropod pest on a host animal, which comprises contacting the pest with an effective amount of a compound of the present invention.

The compounds of Formula (1B) and (2B) can be used to control a wide variety of arthropod pests including various flies and fly larvae, fleas, lice, mites, and ticks. The compounds' ectoparasiticidal activity is achieved when the compounds contact the pests. The contact can be of the egg, larvae, adult, or other life stage. "Contact" includes ingestion of the compound by the pest.

Techniques for delivering ectoparasiticides are well known to those skilled in the art. In general, a present compound is applied to the exterior surface of an animal, whereby it contacts pests already present on the host as well as those which arrive on the host's body within the efficacy period of the compound. Typically, the compound is formulated in a liquid formulation which is sprayed onto the animals surface or poured onto the animal's surface. Another conventional treatment is a "dip", whereby cattle are treated by being substantially immersed in a dilute solution of an ectoparasiticide. For some hosts and pests, the formulation can be a dust, which is sprinkled onto the host, or a shampoo or cream which is employed in bathing the animal. Collars on cats and dogs are also employed as a way of delivering an ectoparasiticide directly to the animal's surface.

In another embodiment, the compounds of the invention can be delivered to animals using ear tags, a delivery method disclosed in U.S. Pat. No. 4,265,876.

In another technique, an ectoparasiticide is applied to locations frequented by animals, so that pests are thereby contacted by the compound even as in direct application to the host. Application to pet bedding is well known, as is application to carpeting. For cattle, dusting bags are well known. These are positioned in a doorway where the cattle inevitably rub against the bag and pests are contacted by the present compound.

In yet another embodiment, the present compounds can be used to control insects and arachnids which are pests in the feces of cattle and other animals. In this embodiment, the compounds are administered orally and the compounds travel through the intestinal tract and emerge in the faces. Control of pests in the feces indirectly protects the animals from the pests.

The compounds are formulated for use as ectoparasiticides in manners known to those skilled in the art. In general, a formulation will include a compound of the present invention and one or more physiologically acceptable adjuvants. Formulations include concentrated versions, in which the present active agent is present in a concentration of from 0.001 to 98.0 percent, with the remaining content being physiologically acceptable carriers. Such formulations, especially those with less than 50 percent of the present compound, can sometimes be used directly, but these formulations can also be diluted with other physiologically acceptable carriers to form more dilute treating formulations. These latter formulations can include the active agent in lesser concentrations of from 0.001 to 0.1 percent.

Human Pharmaceutical Utility

The compounds of the invention are also useful as human pharmaceuticals to control parasites, for example, lice. The compounds can be used, for example, in the formulations for controlling lice that are disclosed in WO 00/01347.

The Anoplura, or sucking lice, are parasites found on nearly all groups of mammals. Of the 15 recognized families of Anoplura, two families, *Pediculidae* and *Pthiridae*, have species found on humans. *Pediculus humanus* is the only species in the family Pediculidae that infests humans. It includes the head louse, *Pediculus humanus capitis*; and the body or clothing louse, *Pediculus humanus humanus*, sometimes called *Pediculus corporis*. The crab louse, *Pthirus pubis*, is a distinct species and is the only member of the family *Pthiridae* that infests humans. As used herein, the term "human lice or louse" includes a member of *Pediculus humanus* or *Pthirus pubis*.

Accordingly, in one of its aspects, the invention provides pediculicidal/ovicidal (anti-lice) formulations for controlling a lice infestation in a human comprising as an active ingredient a spinosyn or a physiologically acceptable derivative or salt thereof, and a physiologically acceptable carrier. Especially useful formulations of this invention are hair-care formulations. Especially useful hair-care formulations are shampoos. The invention also provides methods of using these formulations to control human lice species. These formulations and methods control lice in a safer, more effective manner than previously known anti-lice formulations and methods.

The ant-lice formulations of this invention may be formulated in a number of ways. Particularly useful formulations are shampoos, conditioners, and lotions of the type disclosed in WO 00/01347.

When used in a shampoo formulation, hair conditioner formulation, or lotion the spinosyn component is present at a level of from about 0.1% to about 30%, preferably from about 1% to about 10%.

Specific embodiments contemplated include:
A. a formulation for controlling a lice infestation in a human comprising as an active ingredient a compound of formula (1A) or (2A) where $R^9$ is other than H, or a physiologically acceptable derivative or salt thereof, and a physiologically acceptable carrier;
B. a formulation of embodiment A that is a hair care formulation
C. a pediculicidal shampoo comprising:
   (a) from about 0.1% to about 30% of a compound of formula (1A) or (2A) where $R^9$ is other than H, or a physiologically acceptable derivative or salt thereof;
   (b) from about 5% to about 30% of a synthetic surfactant;
   (c) from about 1% to about 7% of an amide; and
   (d) water;
D. a shampoo of embodiment C wherein the synthetic surfactant is anionic, amphoteric, cationic, zwitterionic, or non-ionic, or a mixture thereof;
E. a shampoo of embodiment D wherein the amide is coconut monoethanolamide, coconut diethanolamide or a mixture thereof;
F. a shampoo of embodiment D additionally comprising from about 1% to about 10% of a non-volatile silicone material;
G. a shampoo of embodiment F wherein the non-volatile silicone is a polyalkyl siloxane, polyalkylaryl siloxane, polyether siloxane co-polymer, or a mixture thereof whose viscosity is from about 100 centipoise to about 150,000,000 centipoise at 25°;
H. a shampoo of embodiment G additionally comprising from about 0.5% to about 5% of a suspending agent selected from the group consisting of crystalline amphiphilic materials having needle-like or platelet structures, polymeric materials, clays, fumed metal oxides, and mixtures thereof,
I. a shampoo of embodiment H wherein the suspending agent is a crystalline amphiphilic material selected from the group consisting of long chain $C_{16}$–$C_{22}$ acyl derivatives, long chain $C_{16}$–$C_{12}$ alkanolamide of fatty acids, and mixtures thereof,
J. a shampoo of embodiment I wherein the suspending agent is an ethylene glycol diester,
K. a shampoo of embodiment D wherein the amount of a spinosyn, or derivative or salt thereof, is at a level from about 0.25% to about 1.5%;
L. a method for controlling a lice infestation in a human comprising topically administering a formulation of embodiment A to the human;
M. the method of embodiment L wherein the lice infestation is *Pediculus humanus capitis;*
N. the method of embodiment L wherein the lice infestation is *Pediculus humanus humanus;*
O. the method of embodiment L wherein the lice infestation is *Pthirus pubis;*
P. a method for treating human hair to kill and facilitate removal of lice and their eggs comprising the steps of:
   (a) applying from about 10 g to about 30 g of a formulation comprising a compound of formula (1A) or (2A) where $R^9$ is other than H, or a physiologically acceptable derivative or salt thereof, and a physiologically acceptable carrier to wet hair;
   (b) working the formulation through the hair and scalp;
   (c) leaving the formulation on the hair and scalp for about 6–10 minutes;

(d) removing the formulation from the hair by rinsing, with water;

Q. the use of a compound of formula (1a) or (2a) where $R^9$ is other than h, or a physiologically acceptable derivative or salt thereof, or a formulation containing either entity, for the manufacture of a medicament for controlling lice in a human.

What is claimed is:

1. A compound of the formulae (1A) or (2A)

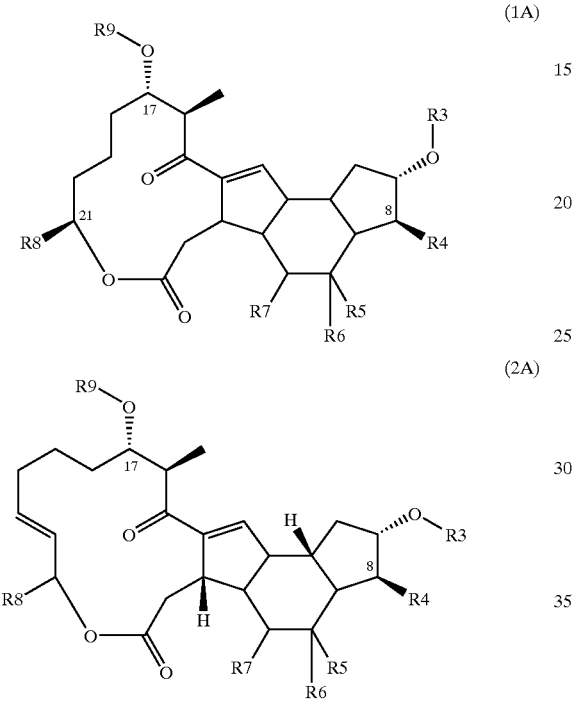

wherein

R3 is a group having one of the following formulas (3a) through (3v)

(3a)

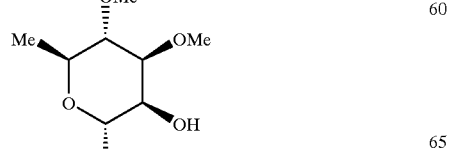

(3b)

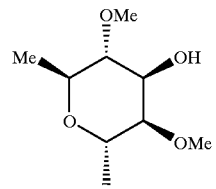

(3c)

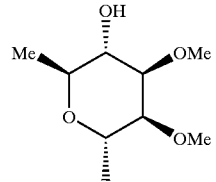

(3d)

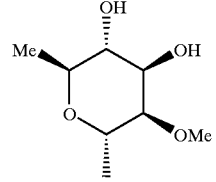

(3e)

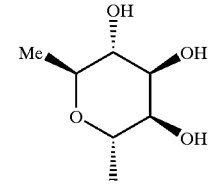

(3f)

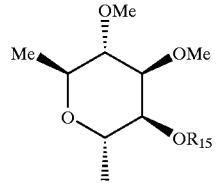

(3g)

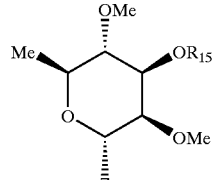

(3h)

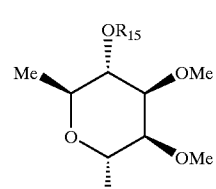

(3i)

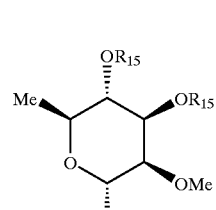

(3j)

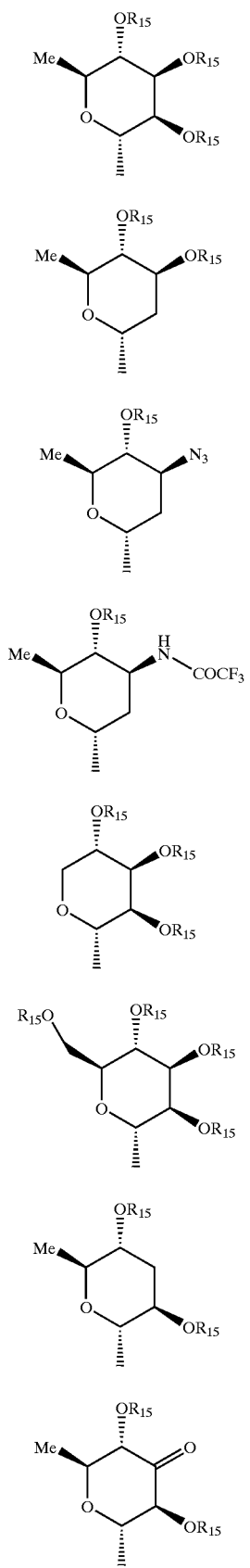
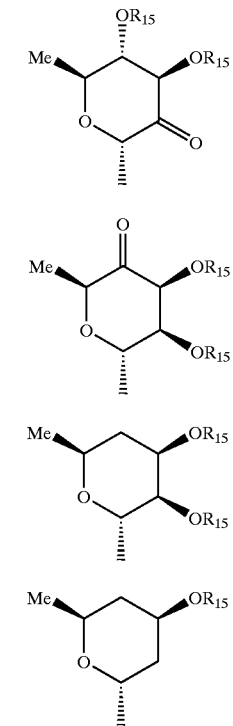

$R^4$ is H, OH, $OR^{15}$, or =O;

$R^5$ is H or $CH_3$;

$R^6$ and $R^7$ are H or combine to form a double bond or combine to form an epoxide group;

$R^8$ in formula (1) is trans-1-butenyl, 1,3-butadienyl, n-butyl, 3-hydroxy-1-butenyl, n-propyl, 1-propenyl, 1,2-epoxy-2-butyl, 3-oxo-1-butenyl, $CH_3CH(OCH_3)CH=CH-$, $CH_3CH(OR^{15})CH=CH-$, $CH_3CH=CHCH(CH_2CO_2Me)-$, or $CH_3CH=CHCH(CH_2CON(Me_2))-$ $R^9$ is H or a group having one of the following formulas (9a) through (9p):

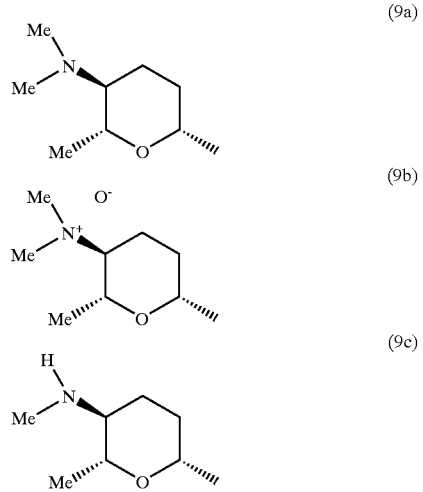

-continued (9d) 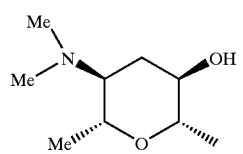

(9e) 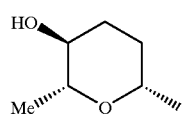

(9f) 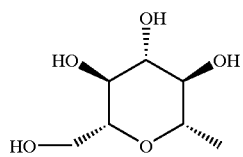

(9g) 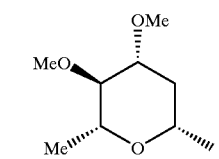

(9h) 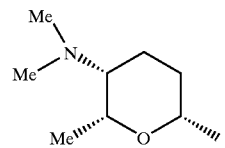

(9i) 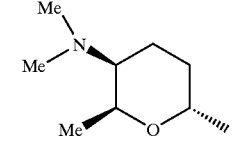

(9j) 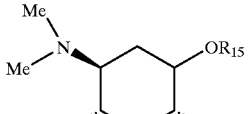

(9k) 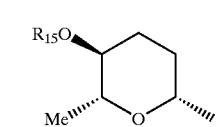

(9l) 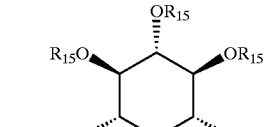

(9m) 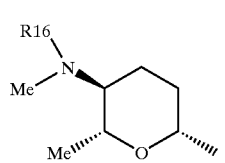

-continued (9n) 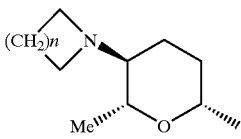

(9o) 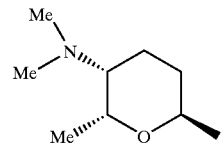

(9p) 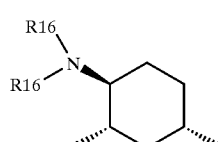

$R^{15}$ is C2–C6 alkyl, C3–C6 branched alkyl, C3–C7 cycloalkyl, C1–C6 alkoxy-C1–C6 alkyl, C1–C6 alkylthio-C1–C6 alkyl, halo C1–C6 alkyl, C2–C6 alkenyl, C2–C6 alkynyl, formyl, C1–C6 alkylcarbonyl, or C3–C6 branched alkylcarbonyl, C3–C7-cycloalkylcarbonyl, C1–C6 alkoxy-C1–C6 alkylcarbonyl, halo C1–C6 alkylcarbonyl, C2–C6 alkenylcarbonyl, C2–C6 alkynylcarbonyl;

$R^{16}$ in formula (9m) is C1–C6 alkyl, C1–C6 alkenyl, formyl, C1–C6 alkylcarbonyl, or C3–C6 branched alkylcarbonyl;

n in formula (9n) is an integer from 1 to 4;

provided that at least one of the following conditions is satisfied:

a) $R^3$ is selected from the group consisting of formulas (3g) to (3v);

b) $R^4$ is —OCH$_3$, —OR$^{15}$ or =O;

c) $R^6$ and $R^7$ are H or $R^6$ and $R^7$ combine to form an epoxide group;

d) $R^8$ is propyl, 1,2-epoxy-1-butyl, CH$_3$C(O)CH=CH—, CH$_3$CH(OCH$_3$)CH=CH—, CH$_3$CH(OR$^{15}$)CH=CH—, CH$_3$CH=CHCH(CH$_2$CO$_2$Me)—, or CH$_3$CH=CHCH(CH$_2$CON(Me$_2$))— e) $R^9$ is selected from the group consisting of formulas (9j) through (9p);

and provided further that the compound 22,23-dihydro-rham-I is excluded.

2. A compound of claim 1 of formula (1) wherein $R^8$ is trans-1-butenyl, 1,3-butadienyl, n-butyl, 3-hydroxy-1-butenyl, n-propyl, 1-propenyl, 1,2-epoxy-1-butyl, 3-oxo-1-butenyl, or CH$_3$COR$^{15}$CH=CH.

3. A compound of claim 1 wherein $R^9$ is other than H.

4. A compound of claim 1 wherein the formula and groups R3, R4, R5, R6, R7, R8, and R9 are present in one of the following combinations:

| formula | R3 | R4 | R5 | R6 | R7 | R8 | R9 |
|---|---|---|---|---|---|---|---|
| (1A) | Me, OMe, OMe, OEt (sugar) | H | H | Double bond | | 1-butenyl | (9a) |
| (1A) | Me, OMe, OEt, OMe (sugar) | H | H | Double bond | | 1-butenyl | (9a) |
| (1A) | Me, OEt, OEt, OMe (sugar) | H | H | Double bond | | 1-butenyl | (9a) |
| (1A) | (3a) | H | H | Double bond | | 3-ethoxy-1-butenyl | (9a) |
| (1A) | (3a) | OC$_2$H$_5$ | H | Double bond | | 1-butenyl | (9a) |
| (1A) | Me, OMe, O-nPr, OMe (sugar) | H | H | Double bond | | 1-butenyl | (9a) |
| (1A) | Me, OMe, O-nBu, OMe (sugar) | H | H | Double bond | | 1-butenyl | (9a) |
| (1A) | Me, OMe, O-allyl, OMe (sugar) | H | H | Double bond | | 1-butenyl | (9a) |
| (1A) | Me, OMe, O-propargyl, OMe (sugar) | H | H | Double bond | | 1-butenyl | (9a) |

| formula | R3 | R4 | R5 | R6 | R7 | R8 | R9 |
|---|---|---|---|---|---|---|---|
| (1A) | Me with OMe, O-iPr, OMe sugar | H | H | Double bond | | 1-butenyl | (9a) |
| (1A) | Me with OMe, O-iBu, OMe sugar | H | H | Double bond | | 1-butenyl | (9a) |
| (1A) | Me with OMe, OCH₂OMe, OMe sugar | H | H | Double bond | | 1-butenyl | (9a) |
| (1A) | Me with OMe, OAc, OMe sugar | H | H | Double bond | | 1-butenyl | (9a) |
| (1A) | Me with OH, OMe, OMe sugar | H | H | H | H | n-Bu | (9a) |
| (1A) | Me with OMe, O-nC₂H₅, OMe sugar | H | H | H | H | n-Bu | (9a) |
| (1A) | Me with OMe, O-C₃H₇, OMe sugar | H | H | H | H | n-Bu | (9a) |

-continued

| formula | R3 | R4 | R5 | R6 | R7 | R8 | R9 |
|---|---|---|---|---|---|---|---|
| (1A) | Me, OMe, O-nC$_4$H$_9$, OMe (pyranose structure) | H | H | H | H | n-Bu | (9a) |
| (1A) | Me, OMe, O-nC$_5$H$_{11}$, OMe (pyranose structure) | H | H | H | H | n-Bu | (9a) |
| (1A) | Me, OMe, O-nC$_2$H$_5$, OMe (pyranose structure) | H | H | Double bond | | 3-OEt-1-butenyl | (9a) |
| (1A) | Me, OMe, O-nC$_3$H$_7$, OMe (pyranose structure) | H | H | Double bond | | 3-O-nPr-1-butenyl | (9a) |
| (1A) | Me, OMe, O-C$_4$H$_9$, OMe (pyranose structure) | H | H | Double bond | | 3-O-nBu-1-butenyl | (9a) |
| (1A) | Me, OMe, O-nC$_2$H$_5$, OMe (pyranose structure) | H | H | H | H | 1-butenyl | (9a) |
| (1A) | Me, OMe, O-nC$_3$H$_7$, OMe (pyranose structure) | H | H | H | H | 1-butenyl | (9a) |

-continued

| formula | R3 | R4 | R5 | R6 | R7 | R8 | R9 |
|---|---|---|---|---|---|---|---|
| (1A) | [structure: Me, OMe, O-nC₄H₉, OMe pyranose] | H | H | H | H | 1-butenyl | (9a) |
| (1A) | (3a) | H | H | H | H | 3-OEt-1-butyl | (9a) |
| (1A) | [structure: Me, dioxolane-fused pyranose, OMe] | H | H | H | H | n-Bu | (9a) |
| (1A) | [structure: Me, OMe, OMe, OEt pyranose] | H | H | H | H | n-Bu | 9(a) |
| (1A) | [structure: Me, OEt, OEt, OMe pyranose] | H | H | H | H | n-Bu | 9(a) |
| (1A) | (3a) | H | H | H | H | n-Bu | 9(a) |
| (1A) | (3a) | H | H | Double bond | | n-Bu | (9a) |
| (1A) | [structure: Me, OMe, OEt, OMe pyranose] | H | H | Double bond | | n-Bu | (9a) |
| (1A) | (3a) | OH | H | H | H | n-Bu | (9a) |
| (1A) | (3a) | H | H | H | H | 1-butenyl | (9a) |
| (1A) | (3a) | OH | H | H | H | 1-butenyl | (9a) |
| (1A) | (3a) | H | H | Double bond | | n-Pr | (9a) |
| (1A) | (3a) | H | H | H | H | n-Pr | (9a) |
| (2A) | (3a) | H | H | H | H | Et | (9a) |
| (1A) | [structure: Me, OMe, OH, OMe pyranose] | H | H | H | H | 1-butenyl | (9a) |

-continued

| formula | R3 | R4 | R5 | R6 | R7 | R8 | R9 |
|---|---|---|---|---|---|---|---|
| (1A) | Me, OMe, OH, OMe (sugar) | H | H | H | H | n-Bu | (9a) |
| (1A) | Me, OMe, OC₂H₅, OMe (sugar) | H | H | H | H | 3-(OC₂H₅)-1-butyl | (9a) |
| (1A) | Me, OMe, OnC₃H₇, OMe (sugar) | H | H | H | H | 3-(O-nC₃H₇)-1-butyl | (9a) |
| (1A) | Me, OMe, OEt, OMe (sugar) | H | H | Double bond | | CH₃CH=CHCH(CH₂CO₂Me)- | (9a) |
| (1A) | Me, OMe, OEt, OMe (sugar) | H | H | Double bond | | CH₃CH=CHCH(CH₂C(O)NMe₂)- | (9a) |
| (1A) | Me, OMe, OnC₄H₉, OMe (sugar) | H | H | H | H | 3-(O-nC₄H₉)-1-butyl | (9a) |
| (1A) | (3a) | H | H | H | H | 3-oxo-1-butyl | (9a) |
| (1A) | (3a) | H | H | H | H | 3-hydroxy-1-butyl | (9a) |
| (1A) | Me, OH, OH, OMe (sugar) | H | H | H | H | n-Bu | (9a) |
| (1A) | (3a) | | H | —O— | | 1-butenyl | (9a) |
| (1A) | (3a) | | H | -O-(alpha epoxide) | | 1-butenyl | H |
| (1A) | (3a) | | H | -O-(beta epoxide) | | 1-butenyl | H |

-continued
| formula | R3 | R4 | R5 | R6 | R7 | R8 | R9 |
|---|---|---|---|---|---|---|---|
| (1A) | (3a) | | H | -O-(beta epoxide) | | 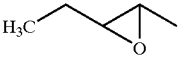 | (9a) |
| (1A) | (3a) | | H | -O-(beta epoxide) | | 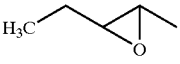 | (9b) |
| (1A) | (3a) | | H | -O-(beta epoxide) | | 1-butenyl | (9b) |
| (1A) | (3a) | | H | H | Double bond | 1-butenyl | 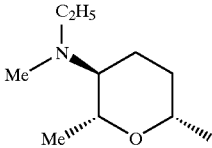 |
| (1A) | (3a) | | H | H | Double bond | 1-butenyl | 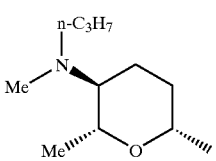 |
| (1A) | (3a) | | H | H | H | n-Bu | 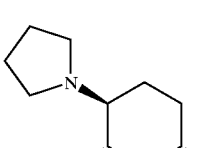 |
| (1A) | (3a) | | H | H | Double bond | 1-butenyl | 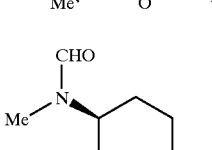 |
| (1A) | (3a) | | H | H | Double bond | 1-butenyl | 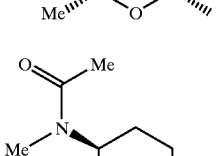 |
| (1A) | (3a) | | H | H | Double bond | n-Bu | (9c) |
| (1A) | 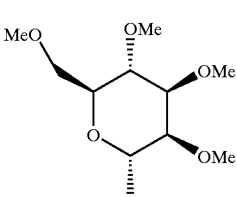 | | H | | Double bond | 1-butenyl | (9a) |
| (1A) | 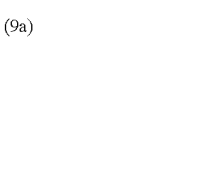 | | H | | Double bond | 1-butenyl | (9a) |

-continued

| formula | R3 | R4 | R5 | R6 | R7 | R8 | R9 |
|---|---|---|---|---|---|---|---|
| (1A) | (sugar with OMe, N₃, Me) | | H | Double bond | | 1-butenyl | (9a) |
| (1A) | (sugar with OEt, OEt, OEt, Me) | | H | Double bond | | 1-butenyl | (9a) |
| (1A) | (sugar with OEt, OEt, Me) | | H | Double bond | | 1-butenyl | (9a) |
| (1A) | (sugar with OMe, OMe, =O, Me) | | H | H | Double bond | 1-butenyl | (9a) |
| (1A) | (sugar with OMe, =O, OMe, Me) | | H | H | Double bond | 1-butenyl | (9a) |
| (1A) | (3a) | =O | H | Double bond | | 1-butenyl | (9a) |
| (1A) | (3a) | H | H | Double bond | | 3-oxo-1-butenyl | (9a) |
| (1A) | (3a) | H | H | Double bond | | 1-butenyl | (Me, O, Me pyranone) |
| (1A) | (sugar with =O, OMe, OMe, Me) | | H | H | Double bond | 1-butenyl | (9a) |
| (1A) | (3a) | | H | H | H | H | 3-oxo-1-butyl | (9a). |

5. A compound of claim 4 wherein the formula and groups R3, R4, R5, R6, R7, R8, and R9 are present in one of the following combinations:

| formula | R3 | R4 | R5 | R6 | R7 | R8 | R9 |
|---|---|---|---|---|---|---|---|
| (1A) | Me with OMe, OMe, OEt sugar | H | H | | Double bond | 1-butenyl | (9a) |
| (1A) | Me with OMe, OEt, OMe sugar | H | H | | Double bond | 1-butenyl | (9a) |
| (1A) | Me with OEt, OEt, OMe sugar | H | H | | Double bond | 1-butenyl | (9a) |
| (1A) | (3a) | H | H | | Double bond | 3-ethoxy-1-butenyl | (9a) |
| (1A) | (3a) | OC$_2$H$_5$ | H | | Double bond | 1-butenyl | (9a) |
| (1A) | Me with OMe, O-nPr, OMe sugar | H | H | | Double bond | 1-butenyl | (9a) |
| (1A) | Me with OMe, O-nBu, OMe sugar | H | H | | Double bond | 1-butenyl | (9a) |
| (1A) | Me with OMe, O-allyl, OMe sugar | H | H | | Double bond | 1-butenyl | (9a) |
| (1A) | Me with OMe, O-propargyl, OMe sugar | H | H | | Double bond | 1-butenyl | (9a) |

-continued

| formula | R3 | R4 | R5 | R6 | R7 | R8 | R9 |
|---|---|---|---|---|---|---|---|
| (1A) | sugar with OMe, OMe, OiPr, Me | H | H | Double bond | | 1-butenyl | (9a) |
| (1A) | sugar with OMe, OMe, OiBu, Me | H | H | Double bond | | 1-butenyl | (9a) |
| (1A) | sugar with OMe, OMe, OCH2OMe, Me | H | H | Double bond | | 1-butenyl | (9a) |
| (1A) | sugar with OMe, OMe, OAc, Me | H | H | Double bond | | 1-butenyl | (9a) |
| (1A) | sugar with OMe, OMe, OEt, Me | H | H | H | H | n-Bu | 9(a) |
| (1A) | sugar with OEt, OEt, OMe, Me | H | H | H | H | n-Bu | 9(a) |
| (1A) | (3a) | H | H | H | H | n-Bu | 9(a) |
| (1A) | (3a) | H | H | Double Bond | | n-Bu | (9a) |
| (1A) | sugar with OMe, OEt, OMe, Me | H | H | Double bond | | n-Bu | (9a) |

-continued

| formula | R3 | R4 | R5 | R6 | R7 | R8 | R9 |
|---|---|---|---|---|---|---|---|
| (1A) | (3a) | OH | H | H | H | n-Bu | (9a) |
| (1A) | (3a) | H | H | H | H | 1-butenyl | (9a) |
| (1A) | (3a) | OH | H | H | H | 1-butenyl | (9a) |
| (1A) | (3a) | H | H | Double bond | | n-Pr | (9a) |
| (2A) | (3a) | H | H | H | H | Et | (9a) |
| (1A) | sugar(Me,OMe,OH,OMe) | H | H | H | H | 1-butenyl | (9a) |
| (1A) | sugar(Me,OMe,OH,OMe) | H | H | H | H | n-Bu | (9a) |
| (1A) | (3a) | | H | —O— | | 1-butenyl | (9a) |
| (1A) | (3a) | | H | -O-(alpha epoxide) | | 1-butenyl | H |
| (1A) | (3a) | | H | -O-(beta epoxide) | | 1-butenyl | H |
| (1A) | (3a) | | H | -O-(beta epoxide) | | H₃C-epoxide | (9a) |
| (1A) | (3a) | | H | -O-(beta epoxide) | | H₃C-epoxide | (9b) |
| (1A) | (3a) | | H | -O-(beta epoxide) | | 1-butenyl | (9b) |
| (1A) | (3a) | H | H | Double bond | | 1-butenyl | N(C₂H₅)(Me)-tetrahydropyran(Me,Me) |
| (1A) | (3a) | H | H | Double bond | | 1-butenyl | N(n-C₃H₇)(Me)-tetrahydropyran(Me,Me) |
| (1A) | (3a) | H | H | H | H | n-Bu | pyrrolidinyl-tetrahydropyran(Me,Me) |
| (1A) | (3a) | H | H | Double bond | | 1-butenyl | N(CHO)(Me)-tetrahydropyran(Me,Me) |

-continued
| formula | R3 | R4 | R5 | R6 | R7 | R8 | R9 |
|---|---|---|---|---|---|---|---|
| (1A) | (3a) | H | H | Double bond | | 1-butenyl | 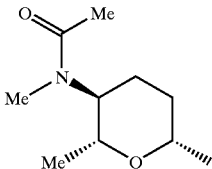 |
| (1A) | (3a) | H | H | Double bond | | n-Bu | (9c) |
| (1A) | 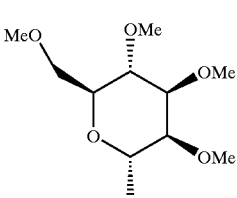 | | H | Double bond | | 1-butenyl | (9a) |
| (1A) | 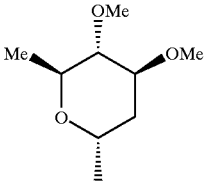 | | H | Double bond | | 1-butenyl | (9a) |
| (1A) | 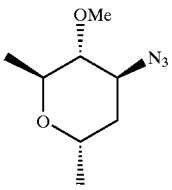 | | H | Double bond | | 1-butenyl | (9a) |
| (1A) | 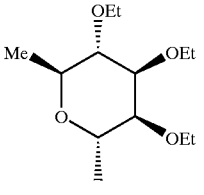 | | H | Double bond | | 1-butenyl | (9a) |
| (1A) | 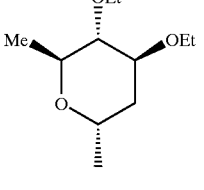 | | H | Double bond | | 1-butenyl | (9a) |
| (1A) | 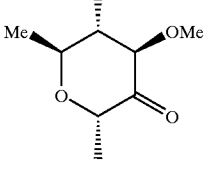 | | H | Double bond | | 1-butenyl | (9a) |

-continued

| formula | R3 | R4 | R5 | R6 | R7 | R8 | R9 |
|---|---|---|---|---|---|---|---|
| (1A) | [structure: tetrahydropyran ring with Me, OMe, =O, OMe substituents] | H | H | Double bond | | 1-butenyl | (9a) |
| (1A) | (3a) | =O | H | Double bond | | 1-butenyl | (9a) |
| (1A) | (3a) | H | H | Double bond | | 3-oxo-1-butenyl | (9a) |
| (1A) | (3a) | H | H | Double bond | | 1-butenyl | [structure: tetrahydropyran ring with =O, Me, Me] |
| (1A) | [structure: tetrahydropyran ring with Me, =O, OMe, OMe] | H | H | Double bond | | 1-butenyl | (9a) |
| (1A) | (3a) | H | H | H | H | 3-oxo-1-butyl | (9a). |

6. A compound of claim 1 having formula 1A wherein R3 is a group of formula (3h), (3j) or (3k).

7. A compound of claim 6 having formula 1A wherein R15 is ethyl, n-propyl, or i-propyl.

8. A compound of claim 6 having formula 1A wherein R6 and R7 are both H.

9. A compound of claim 1 having formula 1A wherein R6 and R7 are both H.

10. A compound of claim 1 having formula 1A wherein R8 is n-butyl.

11. A compound of claim 1 having formula 1A wherein R6 and R7 combine to form an epoxide group.

12. An insecticide or acaricide composition which comprises an insect, mite, or tick inactivating amount of a compound of claim 3 in combination with a phytologically- or physiologically-acceptable carrier.

13. An insecticide or acaricide method which comprises applying to the locus of an insect, mite, or tick inactivating amount of a compound of claim 3.

14. A method of protecting a locus from infestation by insects, mites, or ticks which comprises applying to the locus an insect, mite, or tick inactivating amount of a compound of claim 3.

15. A method of controlling a population of parasites that infest a host animal which comprises administering to the host animal a parasiticidal amount of a compound of claim 3.

16. A method of protecting a plant from infestation by insects, mites or ticks which comprises applying to the soil an insect or mite inactivating amount of a compound of claim 3.

17. A method of controlling a population of parasites that infest a host animal which comprises administering to the host animal a parasiticidal amount of a compound of claim 3.

18. A method of controlling a population of insects which comprises applying to a crop seed an insect-inactivating amount of a compound of claim 3.

19. A method of controlling a population of insects which comprises administering a compound of claim 3 in combination with a second pesticidal material.

20. A formulation for controlling a lice infestation in a human comprising as an active ingredient a compound of claim 3, or a physiologically acceptable derivative or salt thereof, and a physiologically acceptable carrier.

21. A method for controlling a lice infestation in a human comprising topically administering a compound of claim 3 to the human.

* * * * *